(12) United States Patent
Zhan

(10) Patent No.: US 11,445,938 B2
(45) Date of Patent: Sep. 20, 2022

(54) DIAGNOSIS, MONITORING, AND TREATMENT OF RESPIRATORY DISORDERS

(71) Applicant: ResMed Pty Ltd, Bella Vista (AU)

(72) Inventor: Ce Zhan, Sydney (AU)

(73) Assignee: ResMed Pty Ltd

( * ) Notice: Subject to any disclaimer, the term of this patent is extended or adjusted under 35 U.S.C. 154(b) by 982 days.

(21) Appl. No.: 15/504,461

(22) PCT Filed: Aug. 27, 2015

(86) PCT No.: PCT/AU2015/050496
§ 371 (c)(1),
(2) Date: Feb. 16, 2017

(87) PCT Pub. No.: WO2016/029265
PCT Pub. Date: Mar. 3, 2016

(65) Prior Publication Data
US 2017/0367619 A1    Dec. 28, 2017

Related U.S. Application Data

(60) Provisional application No. 62/043,079, filed on Aug. 28, 2014.

(51) Int. Cl.
*A61B 5/087*    (2006.01)
*A61M 16/10*    (2006.01)
(Continued)

(52) U.S. Cl.
CPC ............ *A61B 5/087* (2013.01); *A61B 5/4818* (2013.01); *A61B 5/4836* (2013.01);
(Continued)

(58) Field of Classification Search
CPC ...... A61B 5/087; A61B 5/4818; A61B 5/4836
See application file for complete search history.

(56) References Cited

U.S. PATENT DOCUMENTS 4,944,310 A    7/1990 Sullivan
6,889,691 B2   5/2005 Eklund et al.
(Continued)

FOREIGN PATENT DOCUMENTS

WO    2013020167 A1    2/2013

OTHER PUBLICATIONS

Koley, B., and D. Dey. "Adaptive classification system for real-time detection of apnea and hypopnea events." 2013 IEEE Point-of-Care Healthcare Technologies (PHT). IEEE, 2013. (Year: 2013).*
(Continued)

*Primary Examiner* — Alex M Valvis
*Assistant Examiner* — Yasmeen S Warsi
(74) *Attorney, Agent, or Firm* — Botos Churchill IP Law LLP

(57) ABSTRACT

Automation for a system and/or method detects and/or controls treatment of inspiratory flow limitation. The system may include a flow rate sensor configured to generate a signal representing a respiratory flow rate of a patient. It may include a recording device configured to record the generated respiratory flow rate signal during a diagnosis session. It may include a computing device (7040) configured to detect a degree of inspiratory flow limitation of the patient on the recorded respiratory flow rate signal. The method may include extracting an inspiratory portion of each breath during a detection and/or monitoring session from a respiratory flow rate signal of the patient, calculating a feature vector from each inspiratory flow portion, labelling each feature vector as flow limited or not flow limited, and/or computing a metric based on the labels, the metric indicating the degree of inspiratory flow limitation of the patient during the session.

23 Claims, 27 Drawing Sheets

(51) Int. Cl.
*A61M 16/00* (2006.01)
*A61M 16/16* (2006.01)
*A61B 5/00* (2006.01)

(52) U.S. Cl.
CPC ...... *A61M 16/0066* (2013.01); *A61M 16/026* (2017.08); *A61M 16/109* (2014.02); *A61M 16/1055* (2013.01); *A61M 16/16* (2013.01); *A61M 16/107* (2014.02); *A61M 2016/0027* (2013.01); *A61M 2205/14* (2013.01); *A61M 2205/3368* (2013.01); *A61M 2205/3584* (2013.01); *A61M 2205/3592* (2013.01); *A61M 2205/42* (2013.01); *A61M 2205/502* (2013.01); *A61M 2205/505* (2013.01); *A61M 2209/08* (2013.01)

(56) References Cited

U.S. PATENT DOCUMENTS

| | | | |
|---|---|---|---|
| 7,276,031 | B2 | 10/2007 | Norman et al. |
| 7,866,944 | B2 | 1/2011 | Kenyon et al. |
| 7,882,834 | B2 | 2/2011 | Gradon et al. |
| 8,636,479 | B2 | 1/2014 | Kenyon et al. |
| 8,638,014 | B2 | 1/2014 | Sears et al. |
| 2006/0027234 | A1* | 2/2006 | Gradon ............... A61M 16/024 128/204.21 |
| 2008/0257349 | A1 | 10/2008 | Hedner et al. |
| 2009/0281839 | A1* | 11/2009 | Lynn ..................... G16H 50/70 705/3 |
| 2011/0203588 | A1* | 8/2011 | Armitstead ....... A61M 16/0003 128/204.21 |

OTHER PUBLICATIONS

A. Al Alwani and Y. Chahir, "Neonatal events recognition using LBP descriptor and wavelet thresholding technique," 2014 International Conference on Multimedia Computing and Systems (ICMCS), 2014, pp. 427-432, doi: 10.1109/ICMCS.2014.6911171. (Year: 2014).*
Extended European Search Report and Written Opinion in EP15835731.9 dated Apr. 10, 2018.
Morgenstern C. et al. Assessment of Changes in Upper Airway Obstruction by Automatic Identification of Inspiratory Flow Limitation During Sleep, IEEE Transactions on Biomedical Engineering, vol. 56, No. 8, Aug. 2009 whole document.
International Search Report and Written Opinion for Application No. PCT/AU2015/050496 dated Oct. 19, 2015.
West, John B., Respiratory Physiology, The Essentials, Ninth Edition, Wolters Kluwer, Lippincott William & Wilkins, Published 2011, Copyright 2012 pp. 1-210.

* cited by examiner

DIAGNOSIS, MONITORING, AND TREATMENT OF RESPIRATORY DISORDERS

1 CROSS-REFERENCE TO RELATED APPLICATIONS

The present application is a national phase entry under 35 U.S.C. § 371 of International Application No. PCT/AU2015/050496 filed Aug. 27, 2015, published in English, which claims priority from U.S. Provisional Patent Application No. 62/043,079 Filed Aug. 28, 2014, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, monitoring, treatment, prevention and amelioration of respiratory-related disorders. The present technology also relates to medical devices or apparatus, and their use for these purposes.

5.2 Description of the Related Art

5.2.1 Human Respiratory System and its Disorders

The respiratory system of the body facilitates gas exchange.

The nose and mouth form the entrances to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Sleep Disordered Breathing comprises a wider spectrum of sleep-related breathing abnormalities than OSA. Milder forms of SDB include snoring and upper airway resistance syndrome (UARS). Although the clinical importance of apneas and hypopneas has long been recognized, the importance of UARS in the spectrum of SDB has only recently been recognized. UARS is characterised by Inspiratory Flow Limitation (IFL), which is defined as a lack of increase in airflow rate despite increasing respiratory effort (decreasing intrathoracic pressure). IFL is caused by negative pressure in the upper airway.

5.2.2 Therapy

A range of therapies have been used to treat or ameliorate SDB. Furthermore, otherwise healthy individuals may take advantage of such therapies to prevent respiratory disorders from arising.

Continuous Positive Airway Pressure (CPAP) therapy is a respiratory pressure therapy that has been used to treat OSA and UARS. The mechanism of action is that continuous positive airway pressure acts as a pneumatic splint and reduces upper airway obstruction by pushing the soft palate and tongue forward and away from the posterior oropharyngeal wall.

5.2.3 Treatment Systems

CPAP therapy may be provided by a treatment system or device. A treatment system may comprise a Respiratory Pressure Therapy Device (RPT device), an air circuit, a humidifier, and a patient interface, and data management, as illustrated in FIG. 1.

5.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

5.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above. One known RPT device used for treating sleep disordered breathing is the S9 Sleep Therapy System, manufactured by ResMed Limited.

5.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

5.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

A more convenient diagnosis/monitoring system for home use comprises a nasal cannula, a pressure sensor, a processing device, and recording means. A nasal cannula is a device comprising two hollow open-ended projections that are configured to be inserted non-invasively a little way into a patient's nares so as to interfere as little as possible with the patient's respiration. The hollow projections are in fluid communication with a pressure transducer via a Y-shaped tube. The pressure transducer provides a data signal representative of the pressure at the entrance to the patient's nares (the nasal pressure). It has been shown that nasal pressure is a satisfactory proxy for the nasal flow rate generated by a flow rate transducer in-line with a sealed nasal mask, in that the nasal pressure signal is comparable in both shape and amplitude to a nasal flow rate signal.

The processing device may be configured to analyse the nasal pressure signal from the pressure transducer in real time in order to monitor the patient's condition.

By contrast, diagnosis need not be performed in real time. The recording means is therefore configured to record the nasal pressure signal from the pressure transducer for later off-line analysis by the processing device for diagnosis purposes.

Treatment systems and devices may also be used to diagnose or monitor a condition without treating it. For example, the flow rate signal generated by a flow rate transducer in an RPT device may be analysed in real time or off-line for monitoring or diagnosis purposes.

5.2.5 Diagnosis and Monitoring Methods

Some people affected with the less severe forms of SDB may not be diagnosable using the traditional indicators such as the Apnea-Hypopnea Index (AHI). In particular, pregnant women with mild SDB experience few apneas or hypopneas, and would therefore not be picked up by traditional AHI-based screening. A more sensitive indicator of SDB including its less severe forms is based on Respiratory Effort Related Arousals (RERAs), which consist of multiple episodes of increasing respiratory effort (because of the increased upper airway resistance) resulting in a microarousal. The detection of IFL episodes is necessary to detect RERAs.

Several approaches have been proposed to detect IFL. Early efforts were based on the definition of IFL. These approaches generally measure esophageal (pharyngeal, supraglottic) pressure via a trans-nasal catheter as a proxy for respiratory effort, measure nasal pressure via a cannula as a proxy for flow rate, and identify IFL breaths based on the effort/flow rate relationship. The esophageal pressure based approaches are considered as the "gold-standard" methods for IFL detection. However, they are not commonly used in clinical routine due to their invasiveness and consequent patient discomfort.

More recent work has shown that IFL can be visually identified by human experts purely based on inspection of the flow rate signal, as breaths with IFL present characteristic flow contours (different forms of flattening). Such approaches have the advantage of being non-invasive. To automate this visual inspection process, signal processing techniques such as clustering, artificial neural networks, polynomial modelling, power spectral density analysis, discriminant analysis, support vector machines and Adaboost have been recently employed for automatic IFL detection from flow rate signals, including proxies such as nasal pressure. However, the performance of previous non-invasive methods is not comparable to the gold-standard invasive approaches. One of the reasons is that the signal processing techniques mentioned above are applied either directly to the raw flow rate signal or to the low-pass filtered flow rate signal.

A need therefore exists for a non-invasive method of detecting IFL that is comparable in accuracy to the gold-standard invasive approaches.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to systems and methods used in the diagnosis and monitoring of a respiratory disorder. Another aspect of the present technology relates to systems and methods used in the treatment of a respiratory disorder.

The present technology utilises flow rate signal representations that are particularly suitable for IFL detection. These representations have been chosen and tailored to extract shape and time series features from the inspiratory portions of a flow rate signal. The disclosed systems and methods for non-invasive automatic IFL detection are based on these representations. The disclosed systems and methods may use a nasal cannula/pressure transducer arrangement to generate a signal representative of respiratory flow rate. The disclosed methods treat IFL detection as a binary classification problem, namely labelling the inspiratory portion of a given breath as flow limited or not. Extensive experiments based on different datasets have shown that the detection results of the disclosed methods agree with the visual judgments of expert physicians.

Some versions of the present technology may involve a method of monitoring a patient. The method may include extracting in a processor an inspiratory portion of a breath of the patient from a respiratory flow rate signal of the patient. The flow rate signal may be generated by a flow rate sensor. The method may include calculating in the processor a feature vector from the inspiratory portion. The method may include labelling in the processor the inspiratory portion as flow limited or not flow limited based on the feature vector. The method may include computing in the processor a metric indicating a degree of inspiratory flow limitation of the patient from a plurality of so labelled inspiratory portions during an interval.

Some versions of the present technology may involve a method of treating sleep disordered breathing in a patient. The method may be implemented in one or more processors. The method may include extracting an inspiratory portion of a breath of the patient from a respiratory flow rate signal of the patient. The method may include calculating a feature vector from the inspiratory portion. The method may include labelling the inspiratory portion as flow limited or not flow limited based on the feature vector. The method may include controlling adjustment of a treatment pressure of respiratory pressure therapy being delivered to the patient by a respiratory pressure therapy device, depending on the labelling of the inspiratory portion.

Some versions of the present technology may include an inspiratory flow limitation detection, diagnosis and/or monitoring system. The system may include a flow rate sensor configured to generate a signal representing a respiratory flow rate of a patient. The system may include a computing device, such as a device including one or more processors. The computing device may be configured to extract an inspiratory portion of a breath of the patient from the respiratory flow rate signal. The computing device may be configured to calculate a feature vector from the inspiratory portion. The computing device may be configured to label the inspiratory portion as flow limited or not flow limited based on the feature vector. The computing device may be configured to compute a metric indicating a degree of inspiratory flow limitation of the patient from a plurality of so labelled inspiratory portions during an interval.

Some versions of the present technology may include a sleep disordered breathing treatment system. The system may include a respiratory pressure therapy device configured to deliver respiratory pressure therapy to a patient via a patient interface over an air circuit. The patient interface may be configured to sealingly engage an entrance to an airway of the patient. The air circuit may be in communication with the patient interface. The respiratory pressure therapy device may include a pressure generator configured to generate a supply of air at positive pressure to the air circuit. The respiratory pressure therapy device may include a flow rate sensor configured to generate a signal representing a respiratory flow rate of the patient. The respiratory pressure therapy device may include a controller. The controller may be configured to extract an inspiratory portion of a breath of the patient from the respiratory flow rate signal. The controller may be configured to calculate a feature vector from the inspiratory portion. The controller may be configured to label the inspiratory portion as flow limited or not flow limited based on the feature vector. The controller may be configured to control the pressure generator to adjust a treatment pressure of the respiratory pressure therapy, depending on the labelled inspiratory portion.

Some versions of the present technology may include apparatus for monitoring a patient. The apparatus may include means for extracting an inspiratory portion of a breath of the patient from a respiratory flow rate signal of the patient, the flow rate signal generated by a flow sensor. The apparatus may include means for calculating a feature vector from the inspiratory portion. The apparatus may include means for labelling the inspiratory portion as flow limited or not flow limited based on the feature vector. The apparatus may include means for computing a metric indicating a degree of inspiratory flow limitation of the patient from a plurality of so labelled inspiratory portions during an interval.

According to another aspect of the present technology, there is provided an inspiratory flow limitation detection system. The system comprises a flow rate sensor configured to generate a signal representing a respiratory flow rate of a patient; a recording device configured to record the generated respiratory flow rate signal during a diagnosis session; and a computing device configured to carry out a method of detecting the degree of inspiratory flow limitation of the patient on the recorded respiratory flow rate signal in accordance with the first aspect or any other method or methodology described herein.

The methods/systems/devices/apparatus described herein can provide improved functioning in a processor, such as of a processor of a specific purpose computer, respiratory monitor and/or a respiratory therapy apparatus. Moreover, the methods/systems/devices/apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1 shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5:
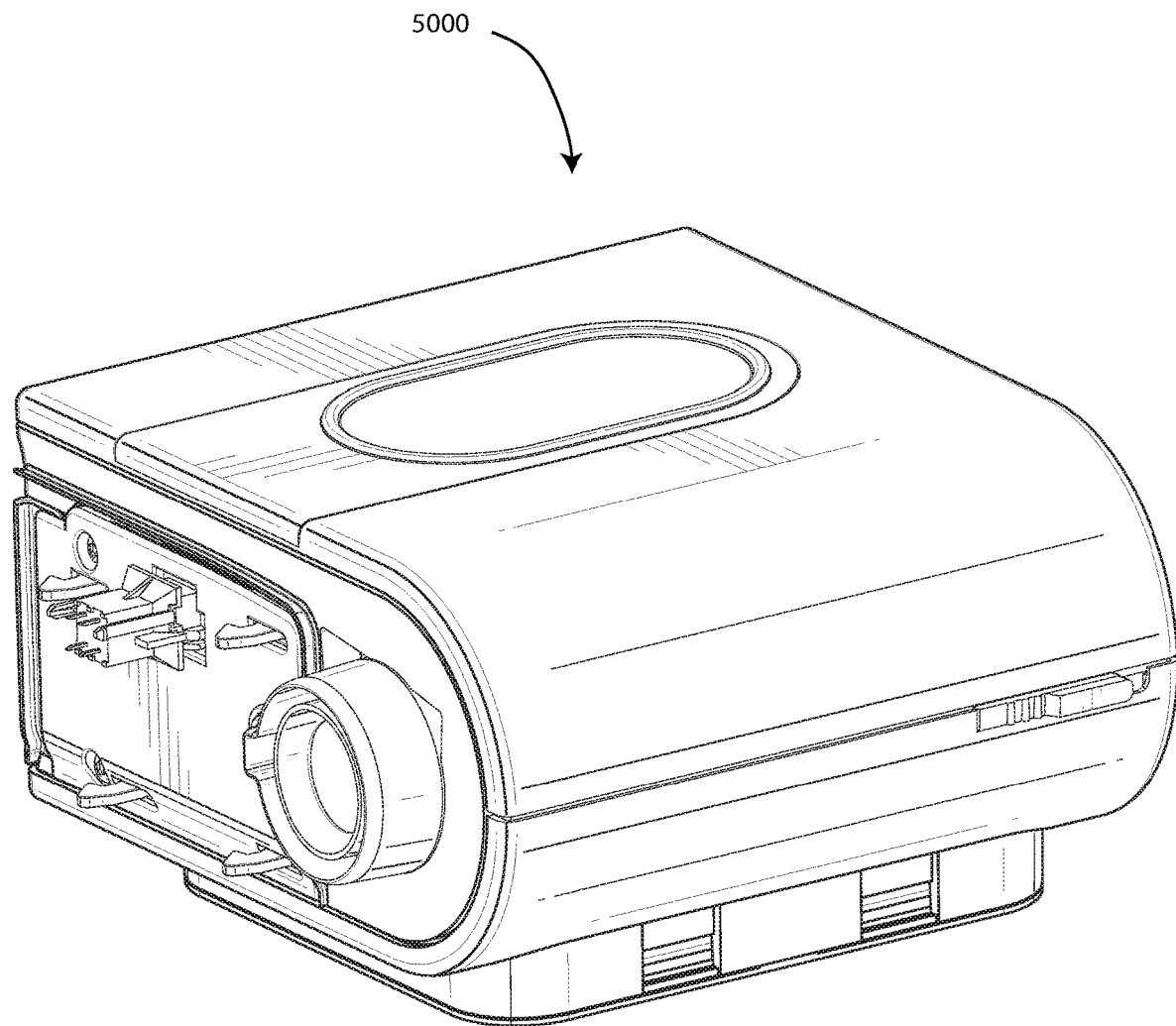

FIG. 5 shows an isometric view of a humidifier in accordance with one form of the present technology.

7.6 Breathing Waveforms

Figure 6A:
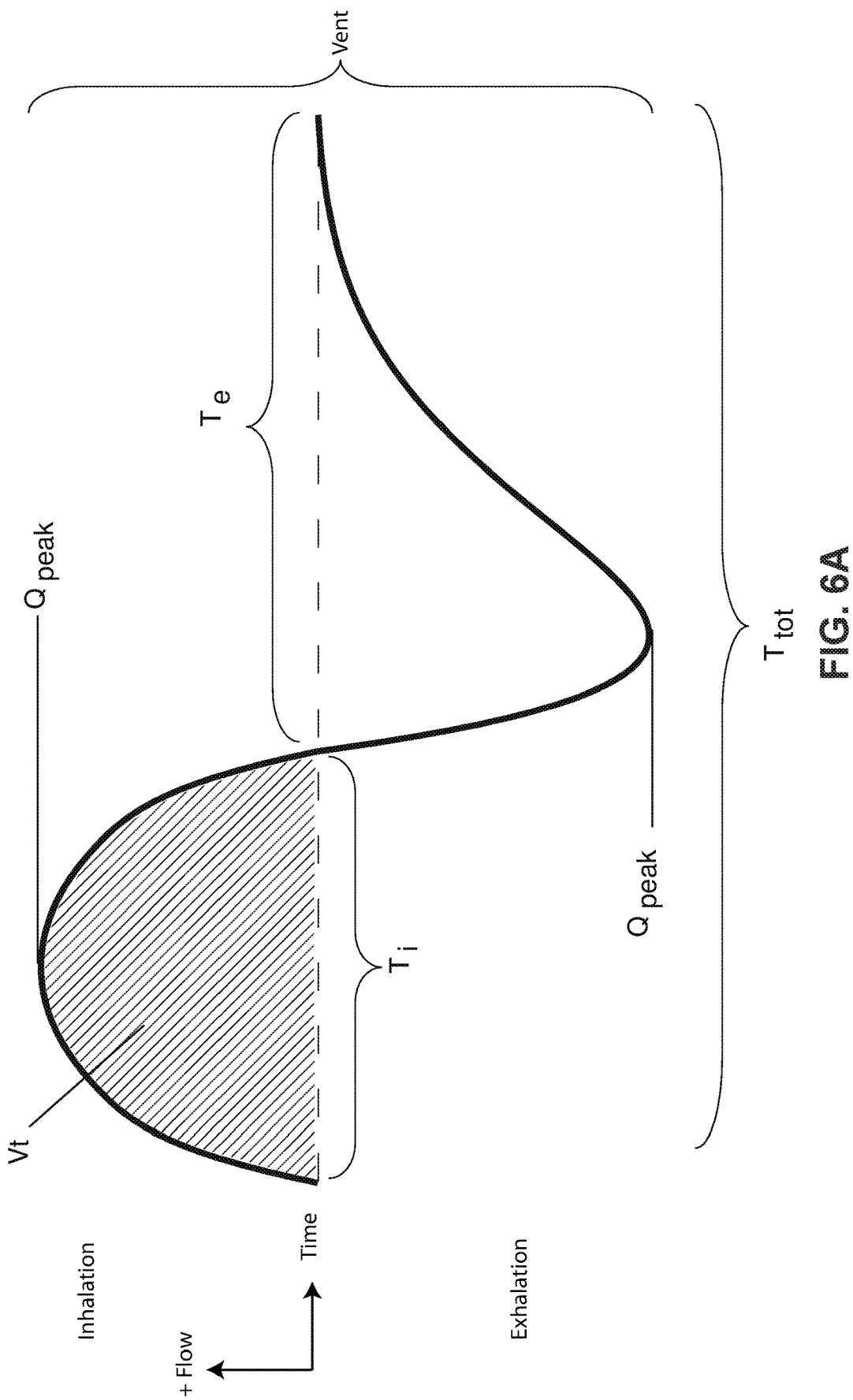

FIG. 6A shows a model typical breath waveform of a person while sleeping.

Figure 6B:
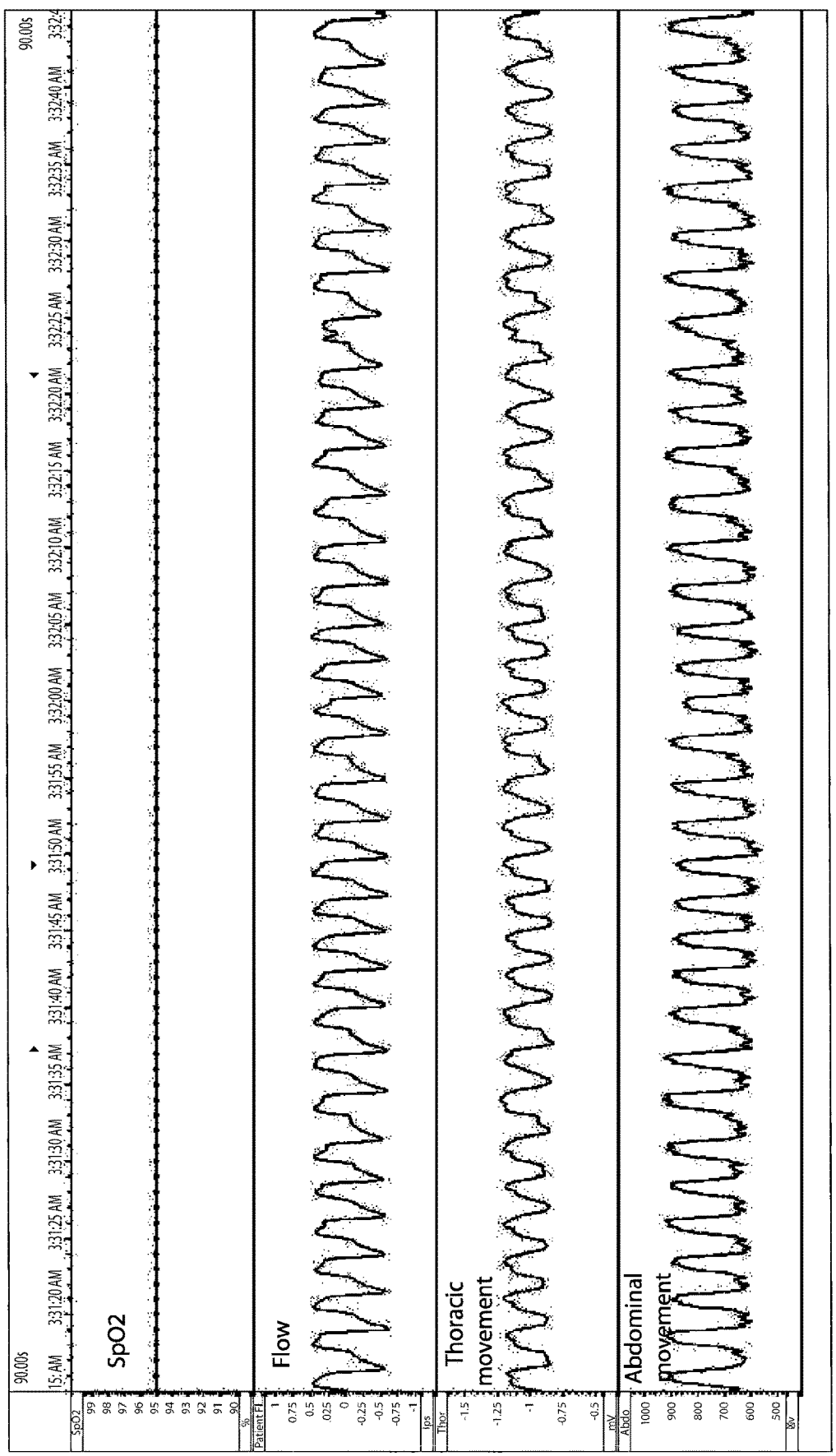

FIG. 6B shows a patient during non-REM sleep breathing normally over a period of about ninety seconds.

Figure 6C:
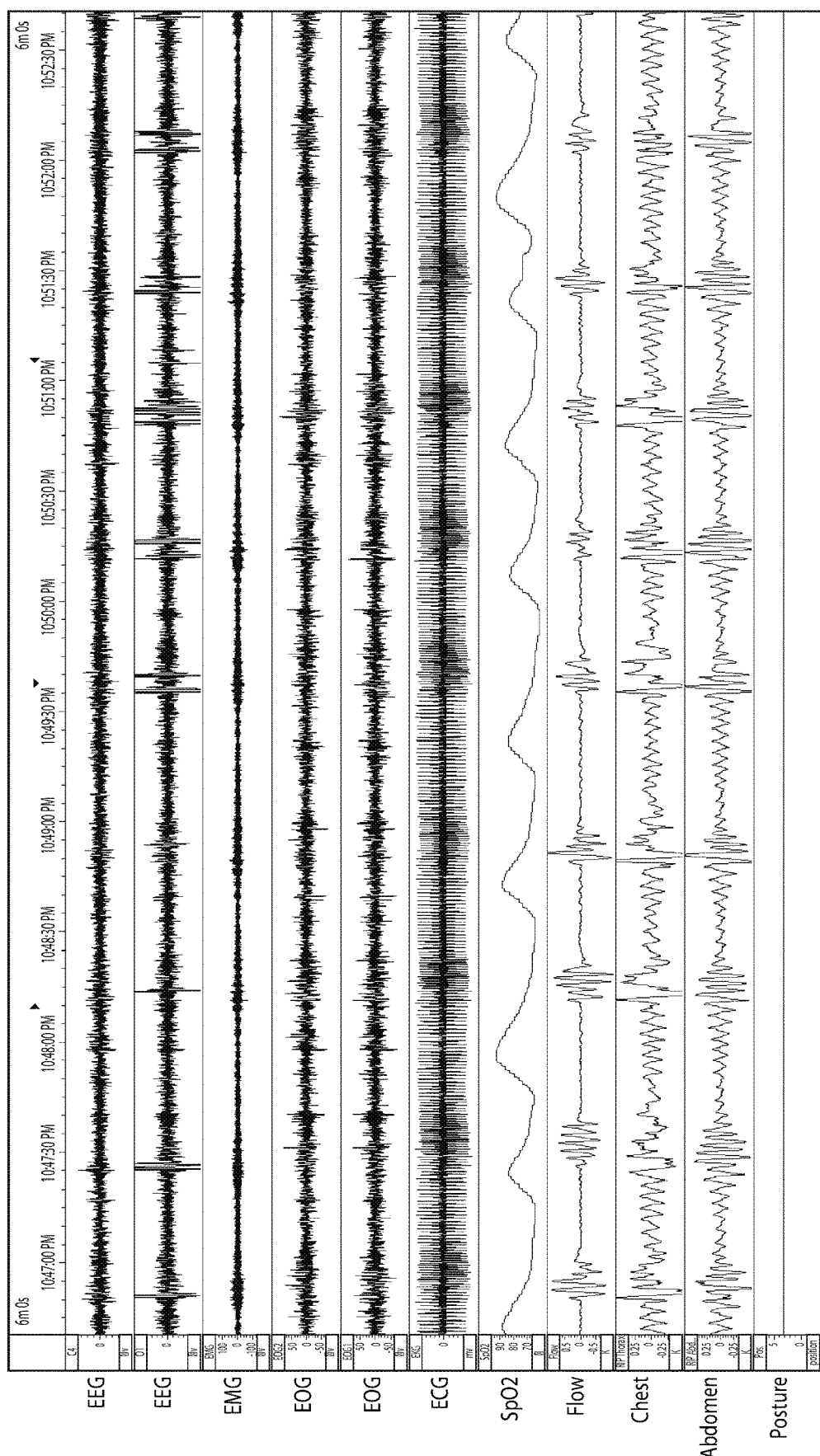

FIG. 6C shows polysomnography of a patient before treatment.

Figure 6D:
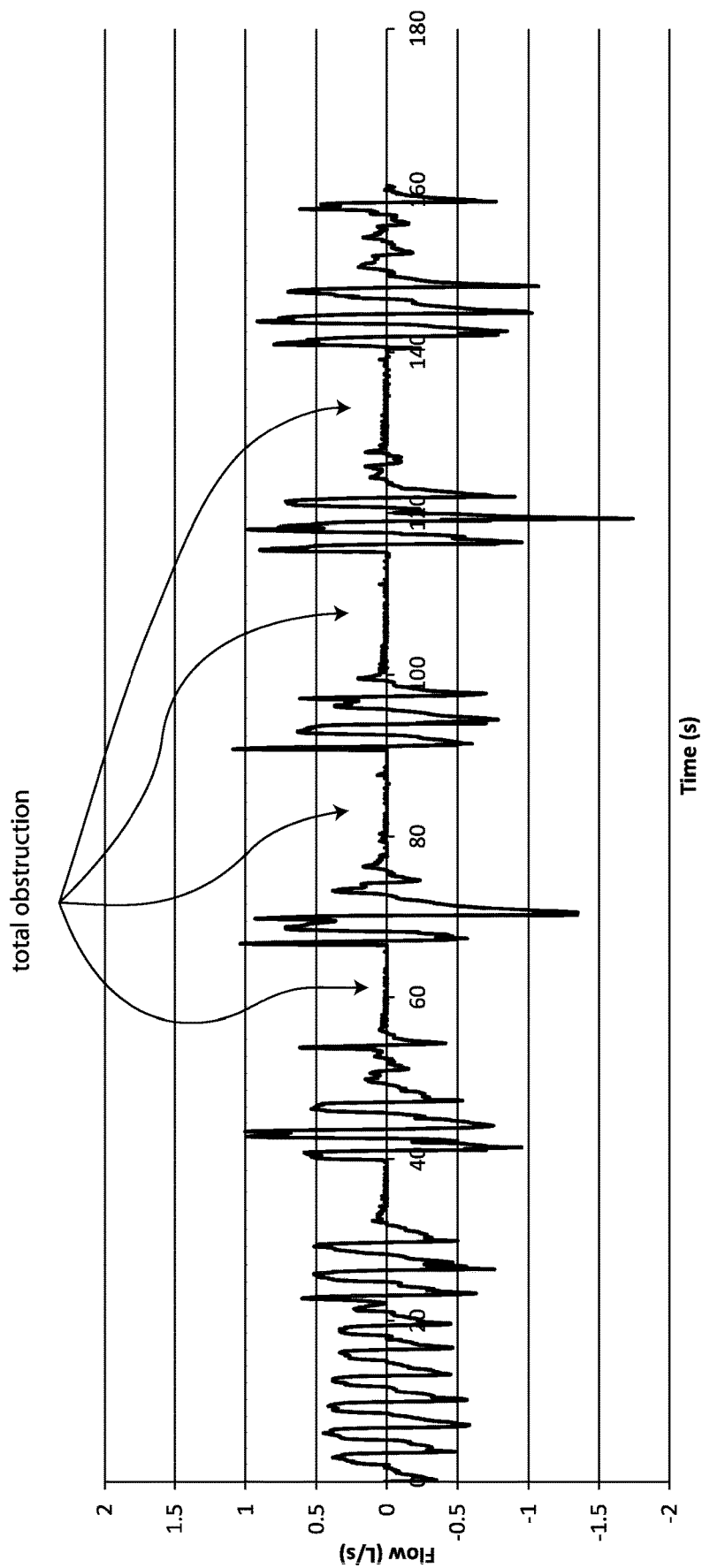

FIG. 6D shows patient flow data where the patient is experiencing a series of total obstructive apneas.

Figure 6E:
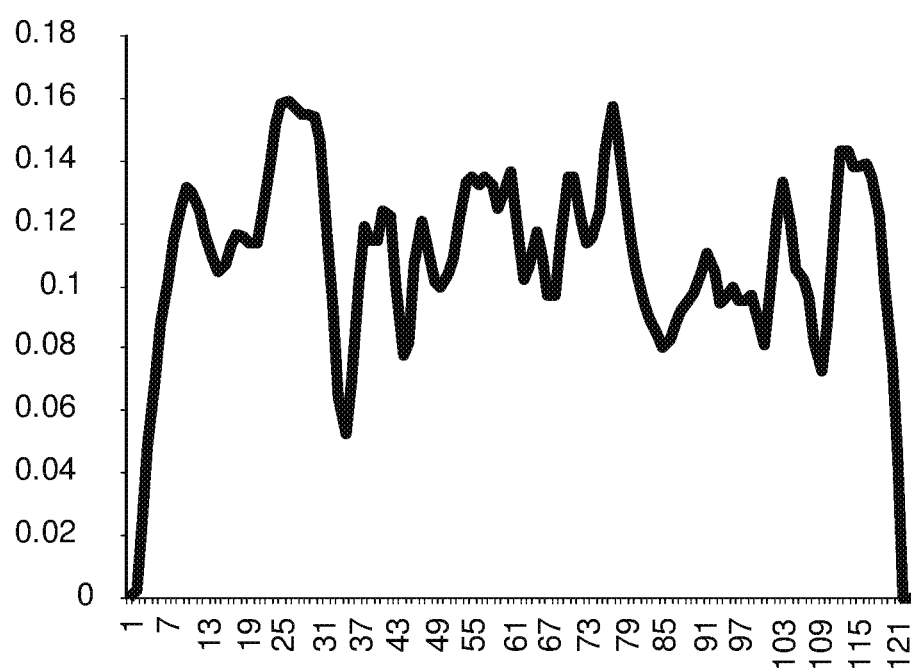

FIG. 6E shows a scaled inspiratory portion of a breath where the patient is experiencing low frequency inspiratory snore.

Figure 6F:
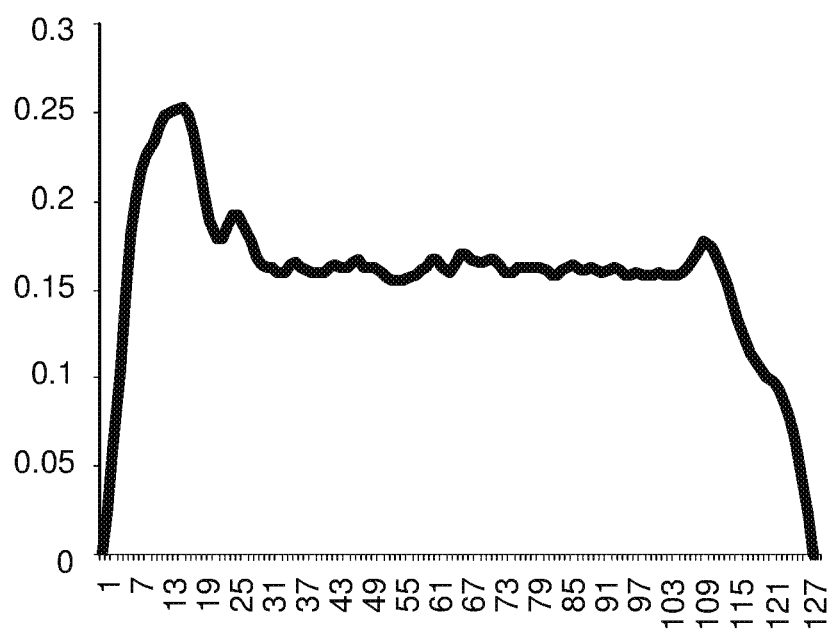

FIG. 6F shows a scaled inspiratory portion of a breath where the patient is experiencing an example of flattened inspiratory flow limitation.

Figure 6G:
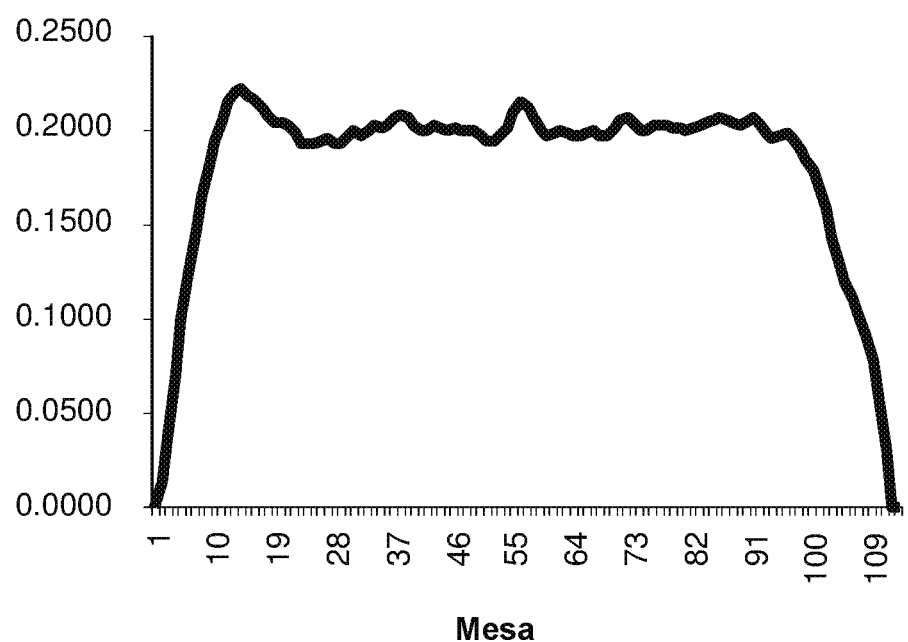

FIG. 6G shows a scaled inspiratory portion of a breath where the patient is experiencing an example of "mesa" flattened inspiratory flow limitation.

Figure 6H:
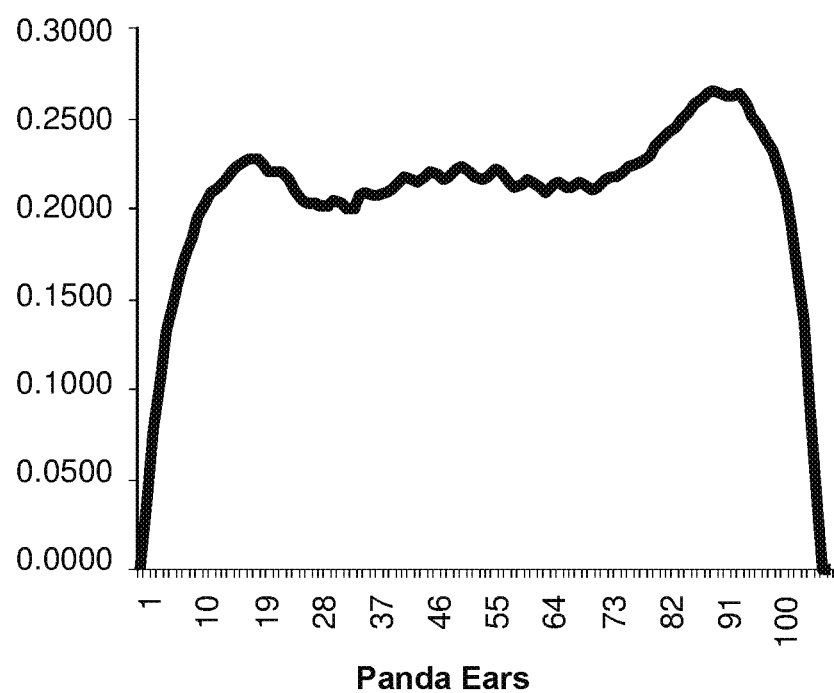

FIG. 6H shows a scaled inspiratory portion of a breath where the patient is experiencing an example of "panda ears" inspiratory flow limitation.

Figure 6I:
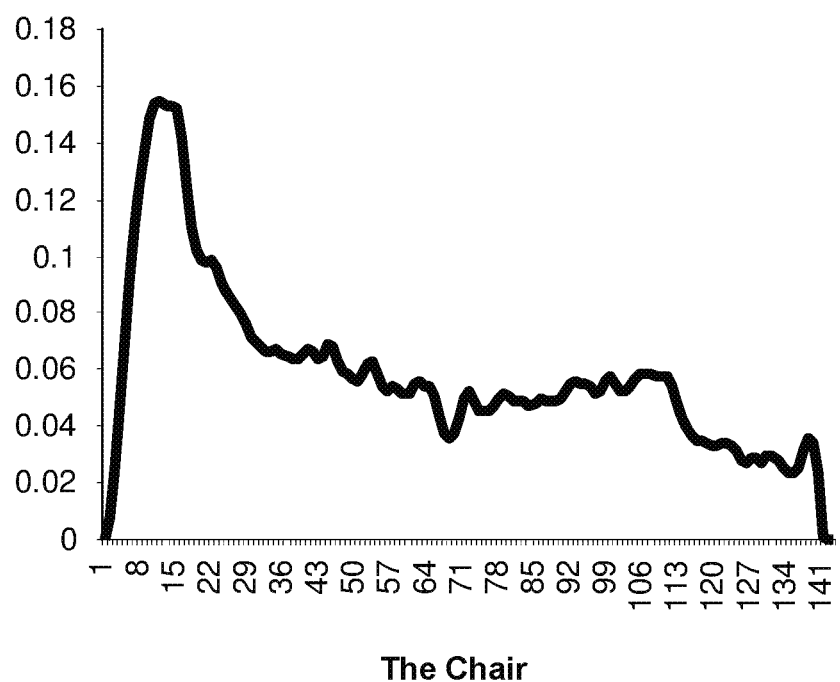

FIG. 6I shows a scaled inspiratory portion of a breath where the patient is experiencing an example of "chair" inspiratory flow limitation.

Figure 6J:
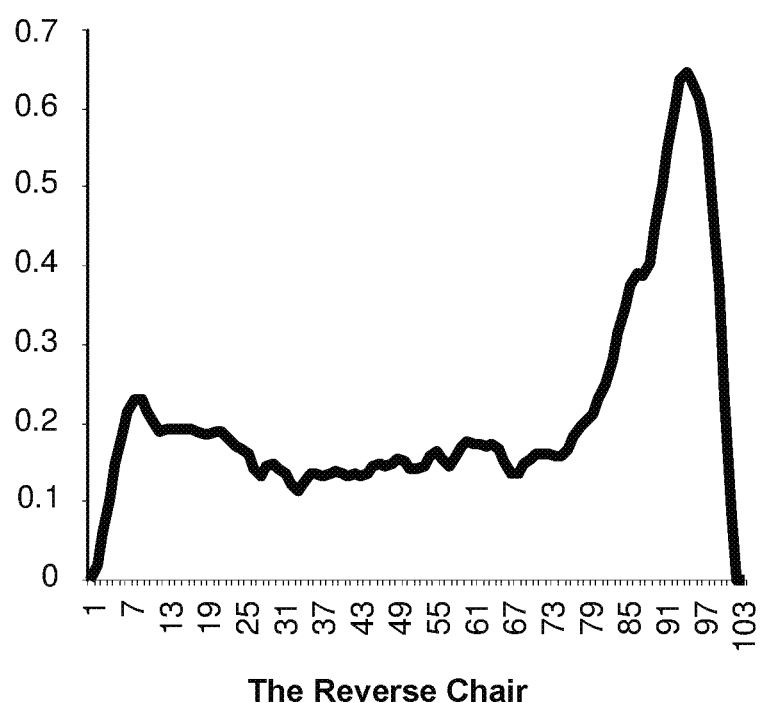

FIG. 6J shows a scaled inspiratory portion of a breath where the patient is experiencing an example of "reverse chair" inspiratory flow limitation.

Figure 6K:
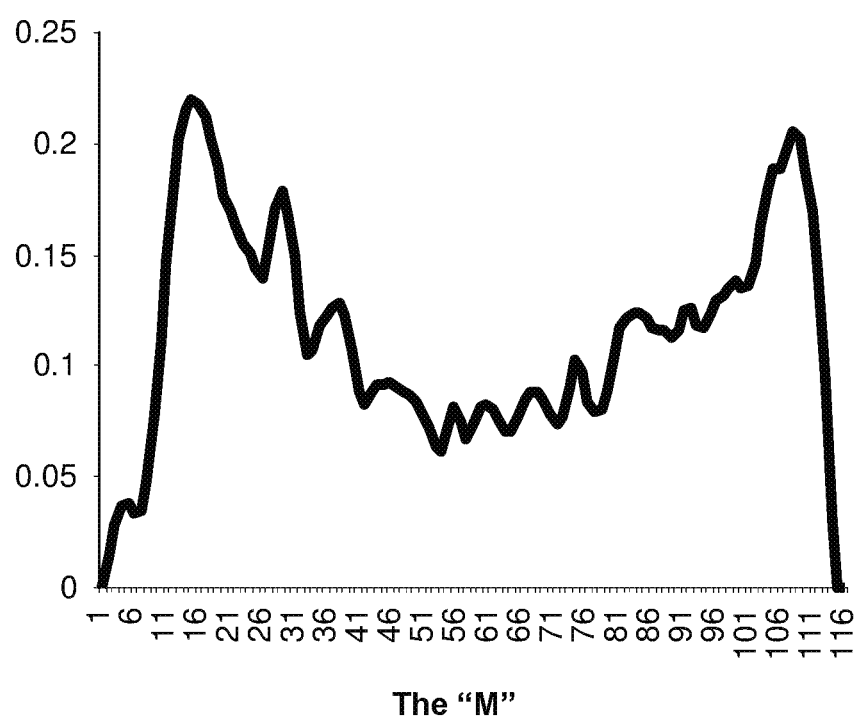

FIG. 6K shows a scaled inspiratory portion of a breath where the patient is experiencing an example of "M-shaped" inspiratory flow limitation.

Figure 6L:
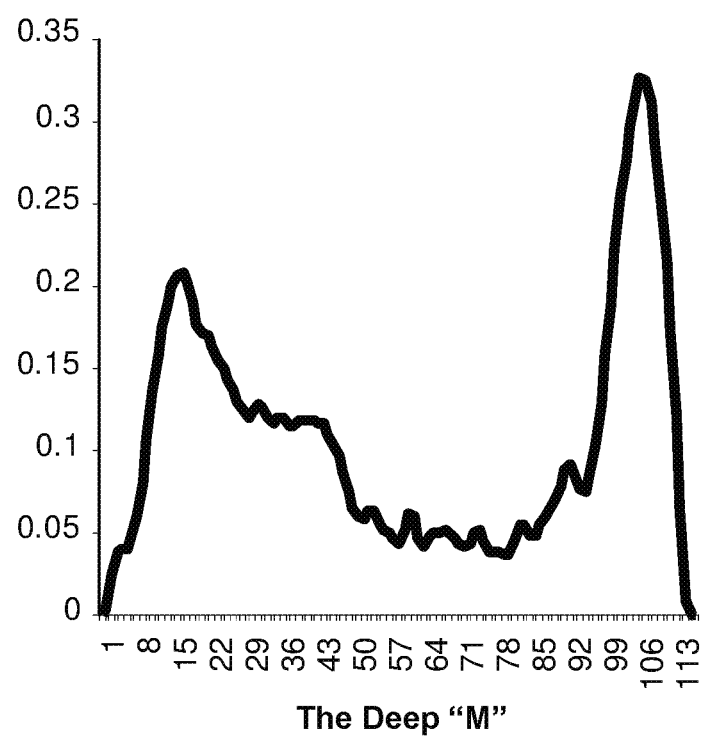

FIG. 6L shows a scaled inspiratory portion of a breath where the patient is experiencing an example of severely "M-shaped" inspiratory flow limitation.

7.7 Diagnosis and Monitoring Systems and Methods

Figure 7A:
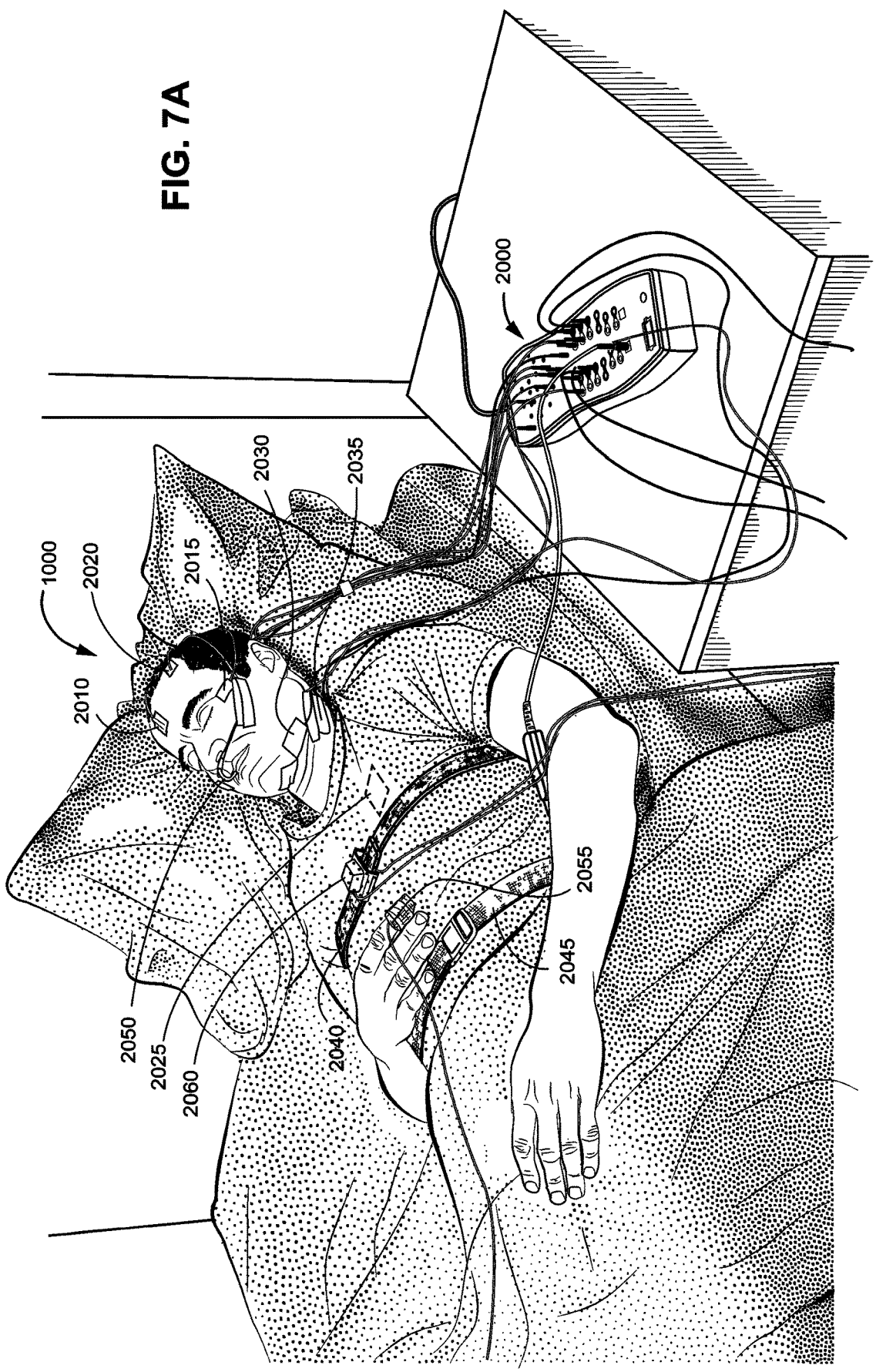

FIG. 7A shows a patient 1000 undergoing polysomnography. The patient 1000 is wearing an oro-nasal cannula 2050 connected to a headbox 2000 containing a pressure transducer (not shown). A polysomnography system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

Figure 7B:
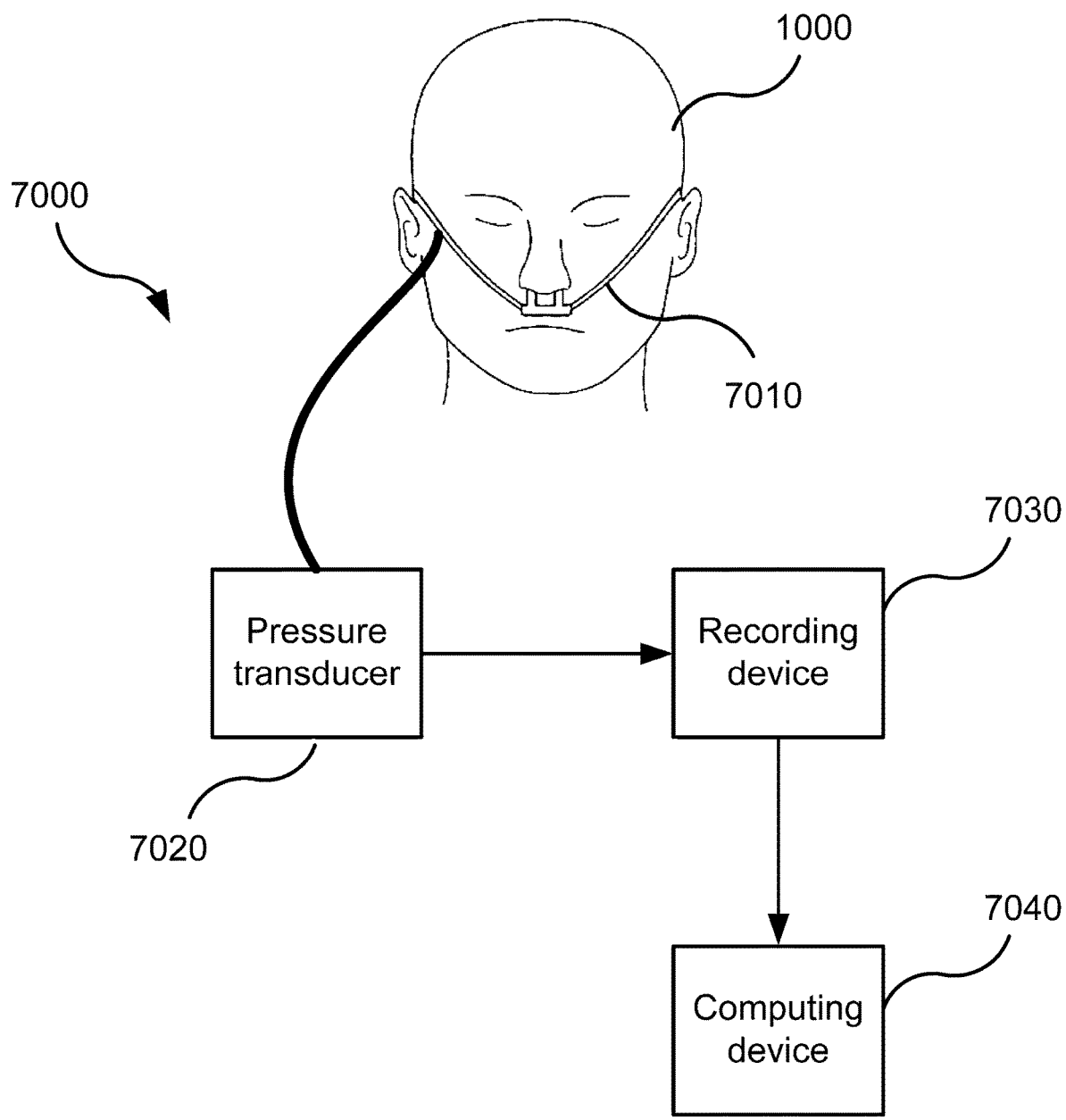

FIG. 7B is a block diagram of a system for diagnosing SDB according to one form of the present technology.

Figure 7C:
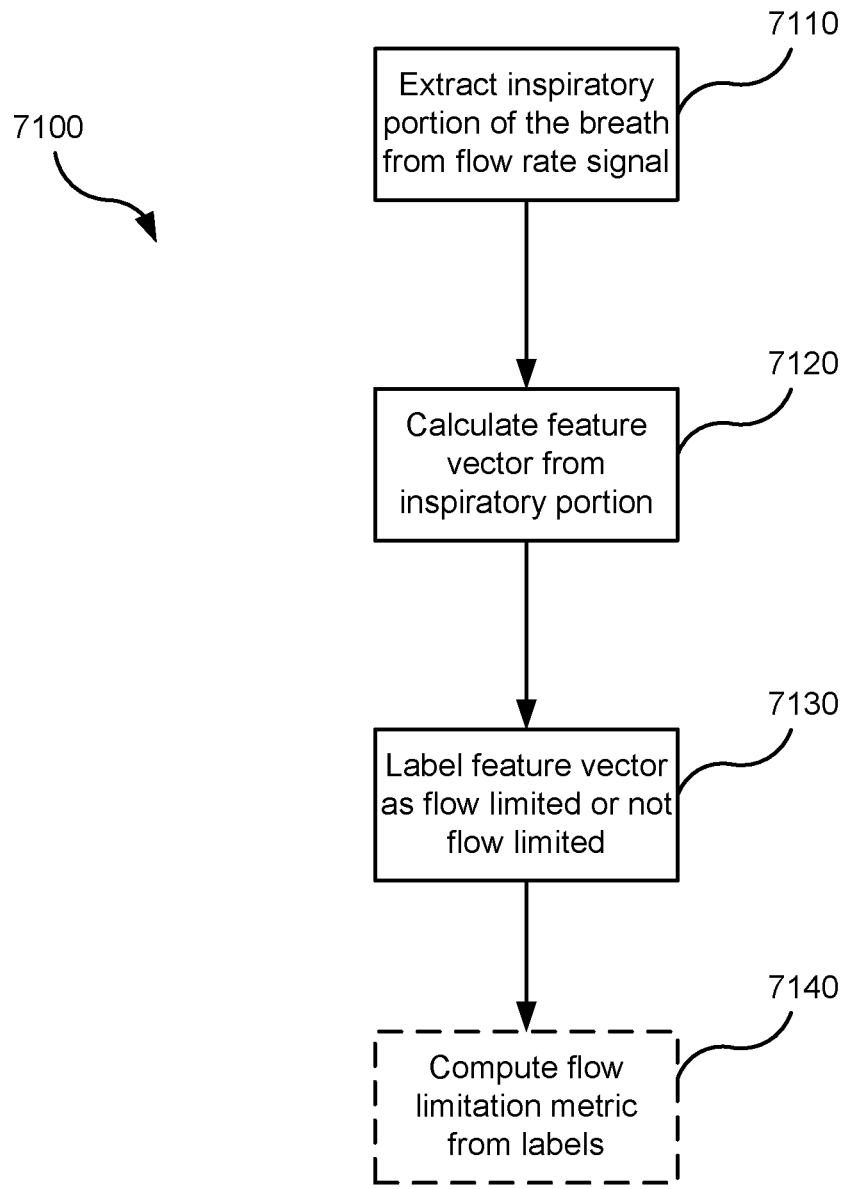

FIG. 7C is a flow chart illustrating a method of diagnosis or monitoring of inspiratory flow limitation.

Figure 7D:
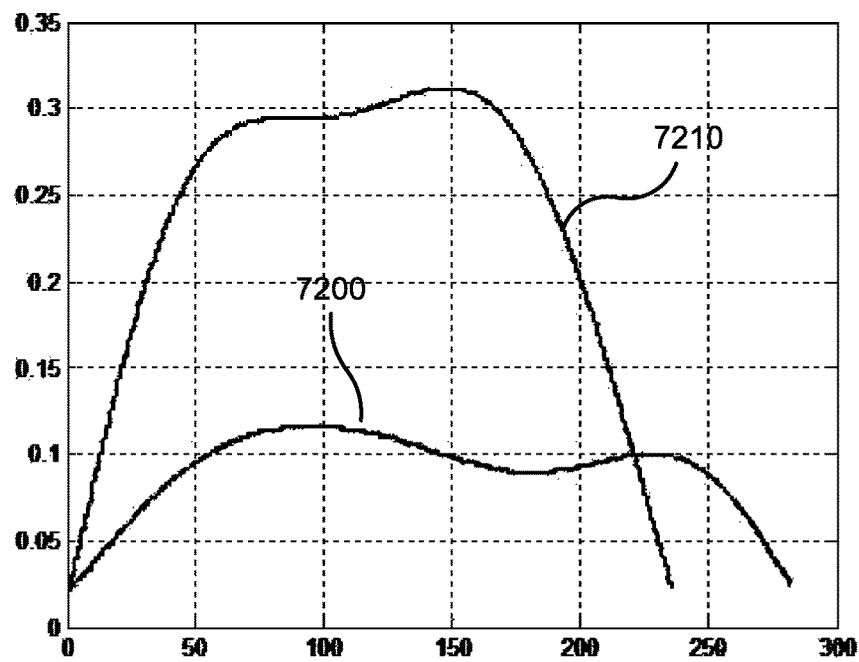

FIG. 7D shows an inspiratory portion with flow limitation, and an inspiratory portion of a normal breath.

Figure 7E:
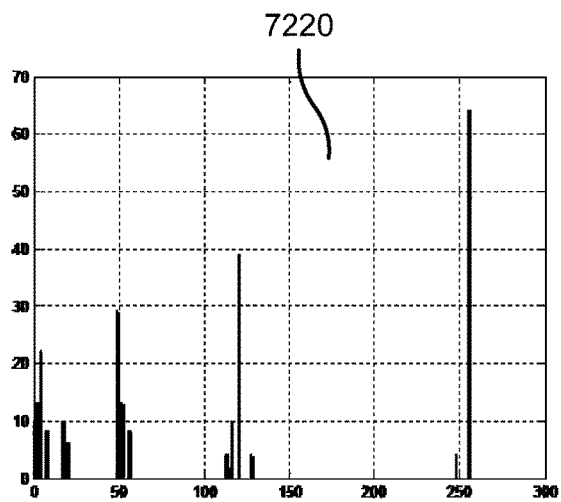

FIG. 7E shows a histogram of the difference-based local binary pattern of the flow-limited inspiratory portion of FIG. 7D.

Figure 7F:
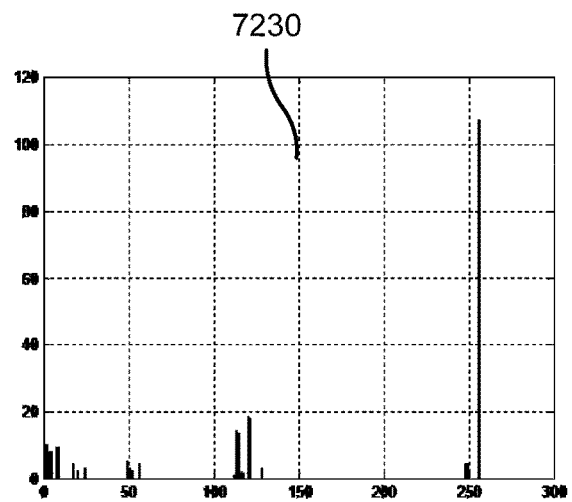

FIG. 7F shows a histogram of the difference-based local binary pattern of the normal inspiratory portion of FIG. 7D.

Figure 7G:
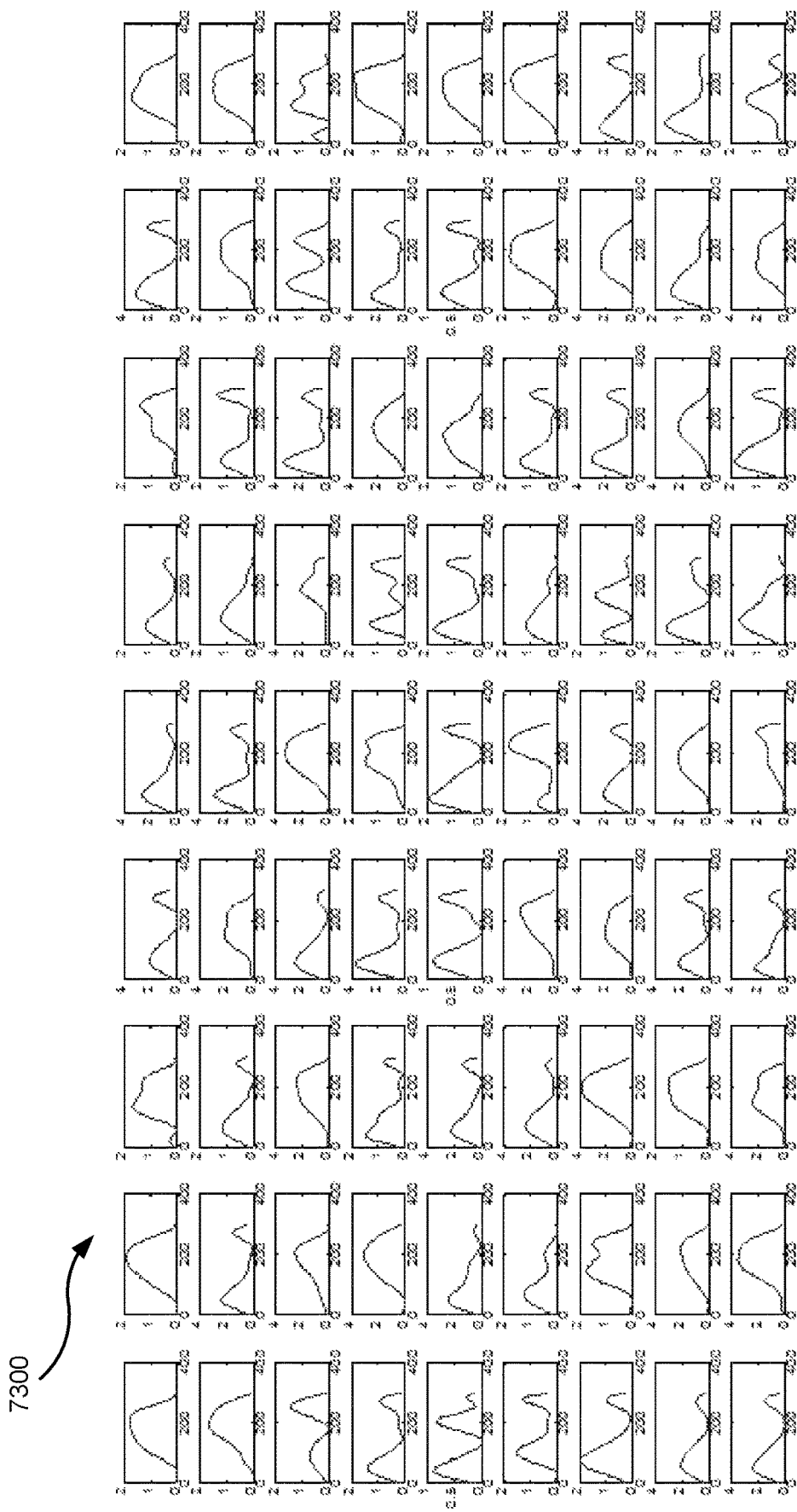

FIG. 7G shows a set of basis vectors obtained using sparsity-constrained non-negative matrix factorisation.

Figure 7H:
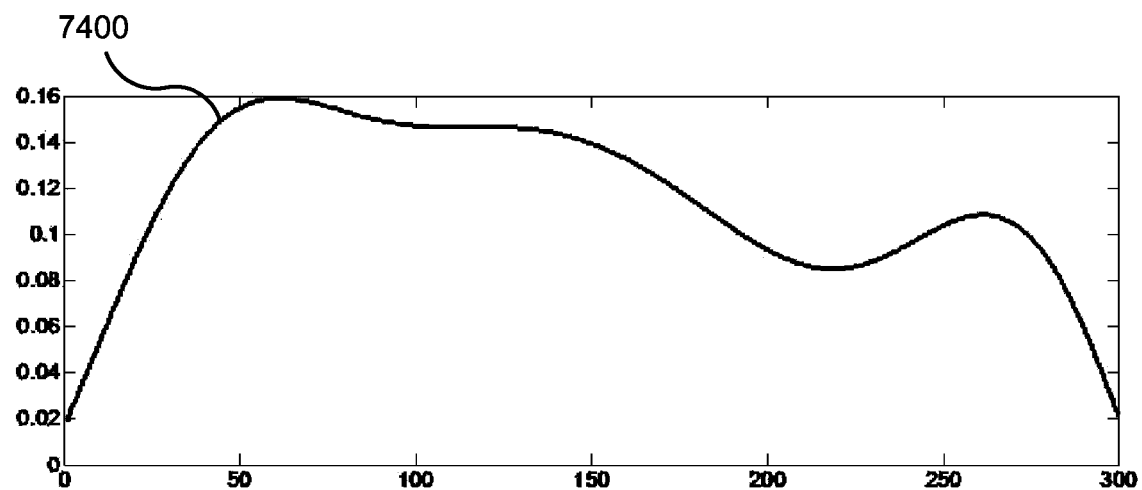

FIG. 7H shows an example inspiratory portion.

Figure 7I:
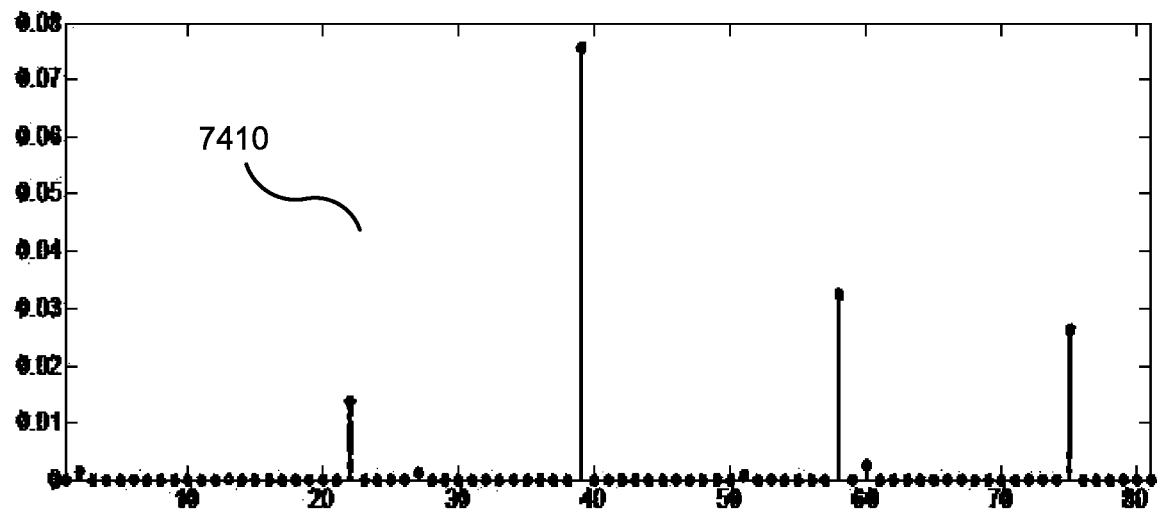

FIG. 7I is a plot of the coefficients of the inspiratory portion of FIG. 7H using the basis vectors of FIG. 7G.

Figure 7J:
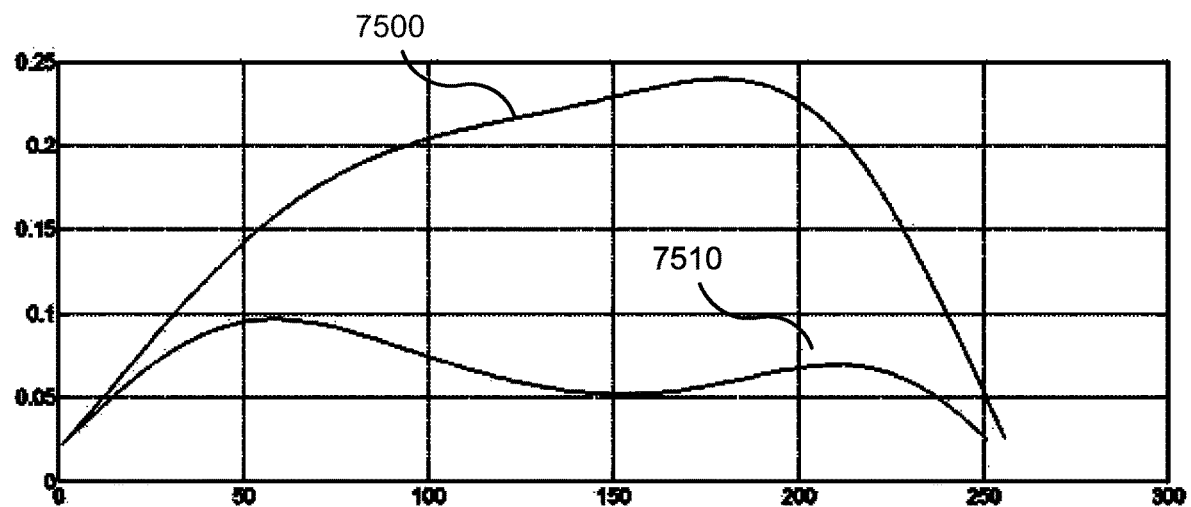

FIG. 7J shows an example normal inspiratory portion and a flow-limited inspiratory portion.

Figure 7K:
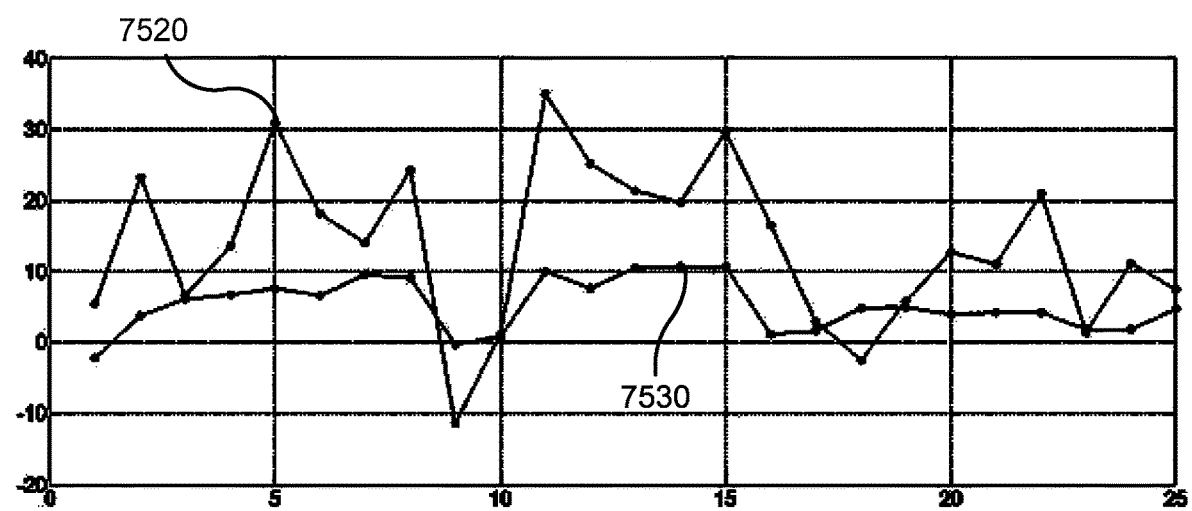

FIG. 7K is a plot of the 25 entries of the DF feature vectors of the inspiratory portions of FIG. 7J.

7.8 Treatment Methods

Figure 1:
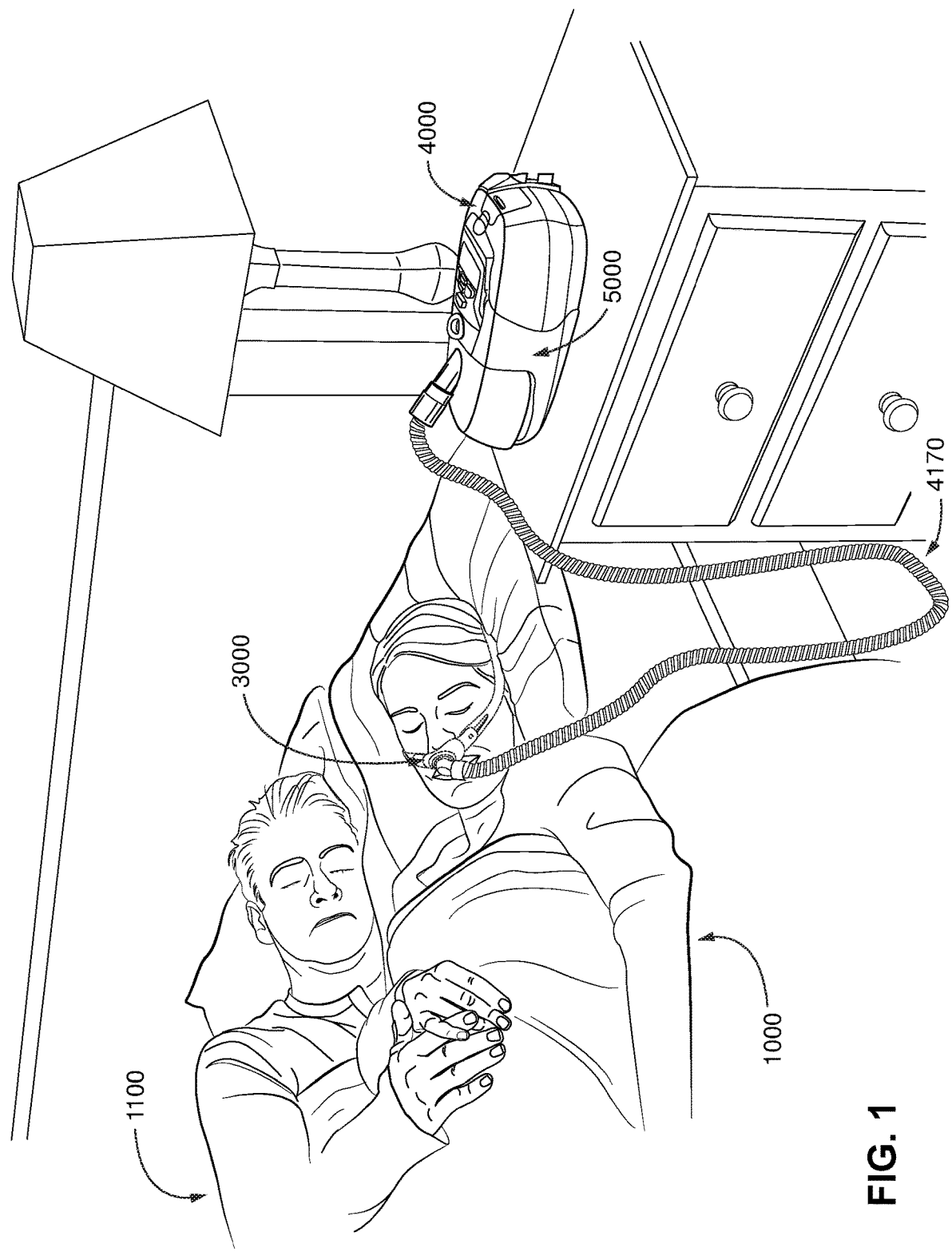
Figure 2:
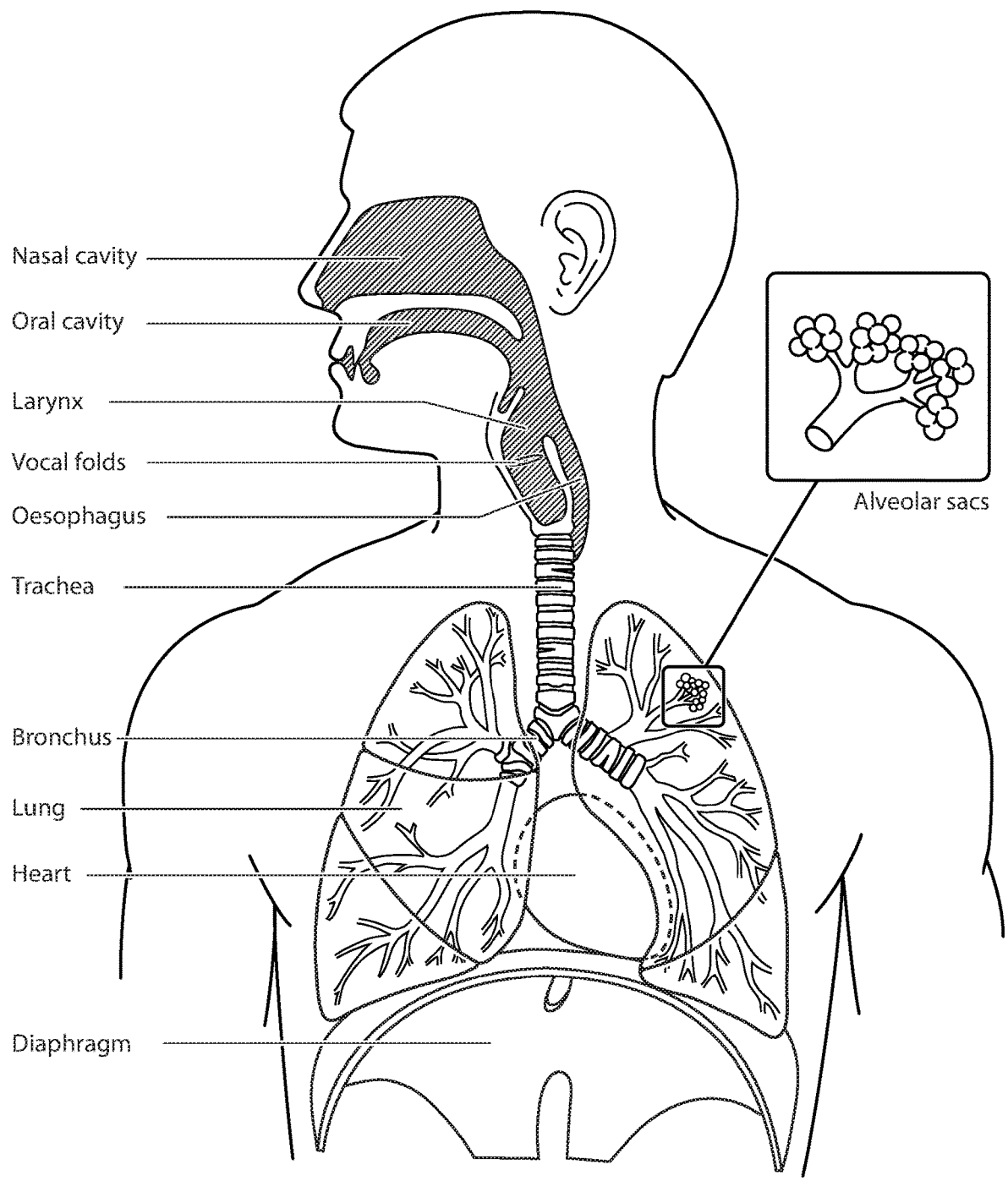
Figure 3:
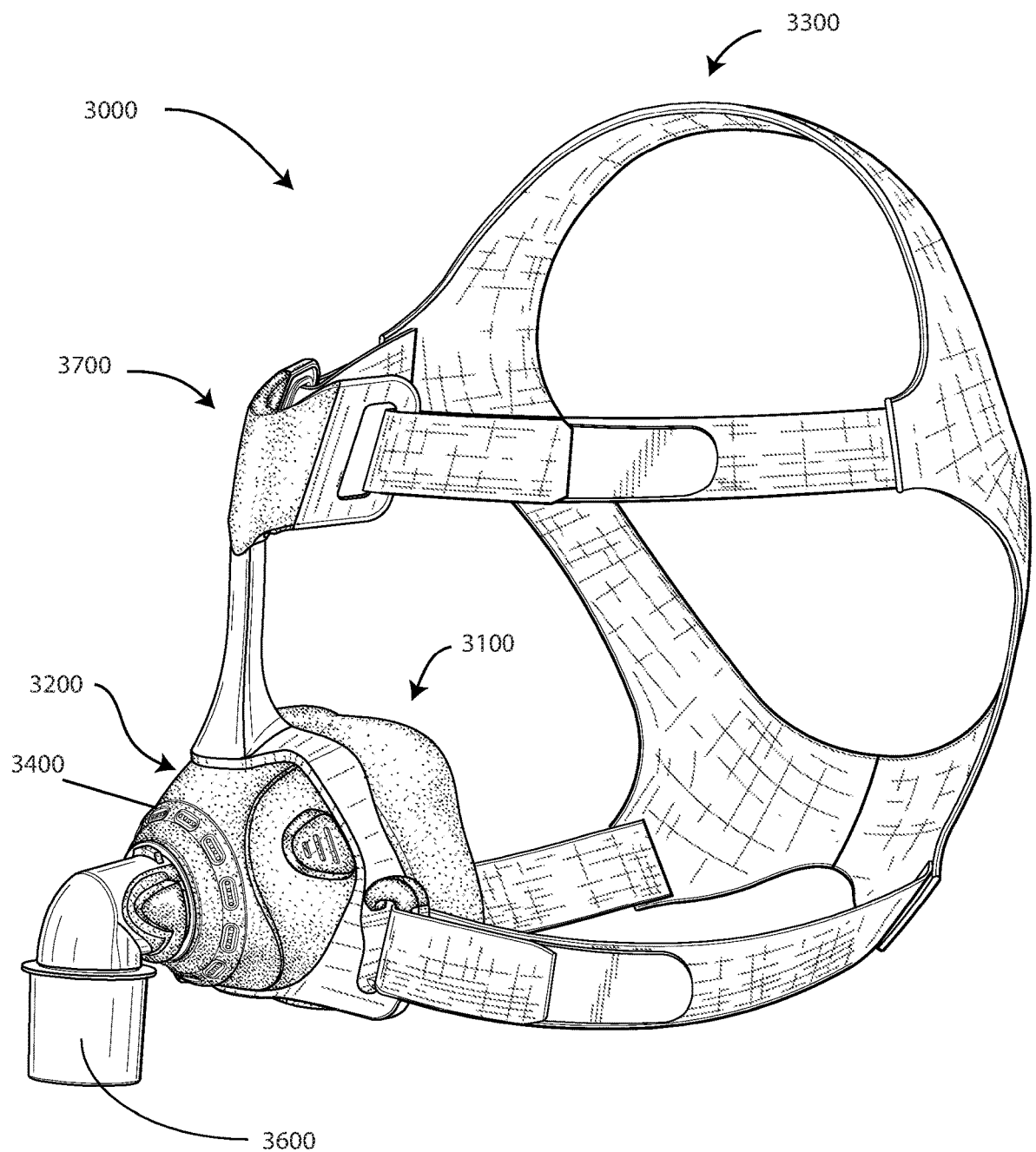
Figure 4A:
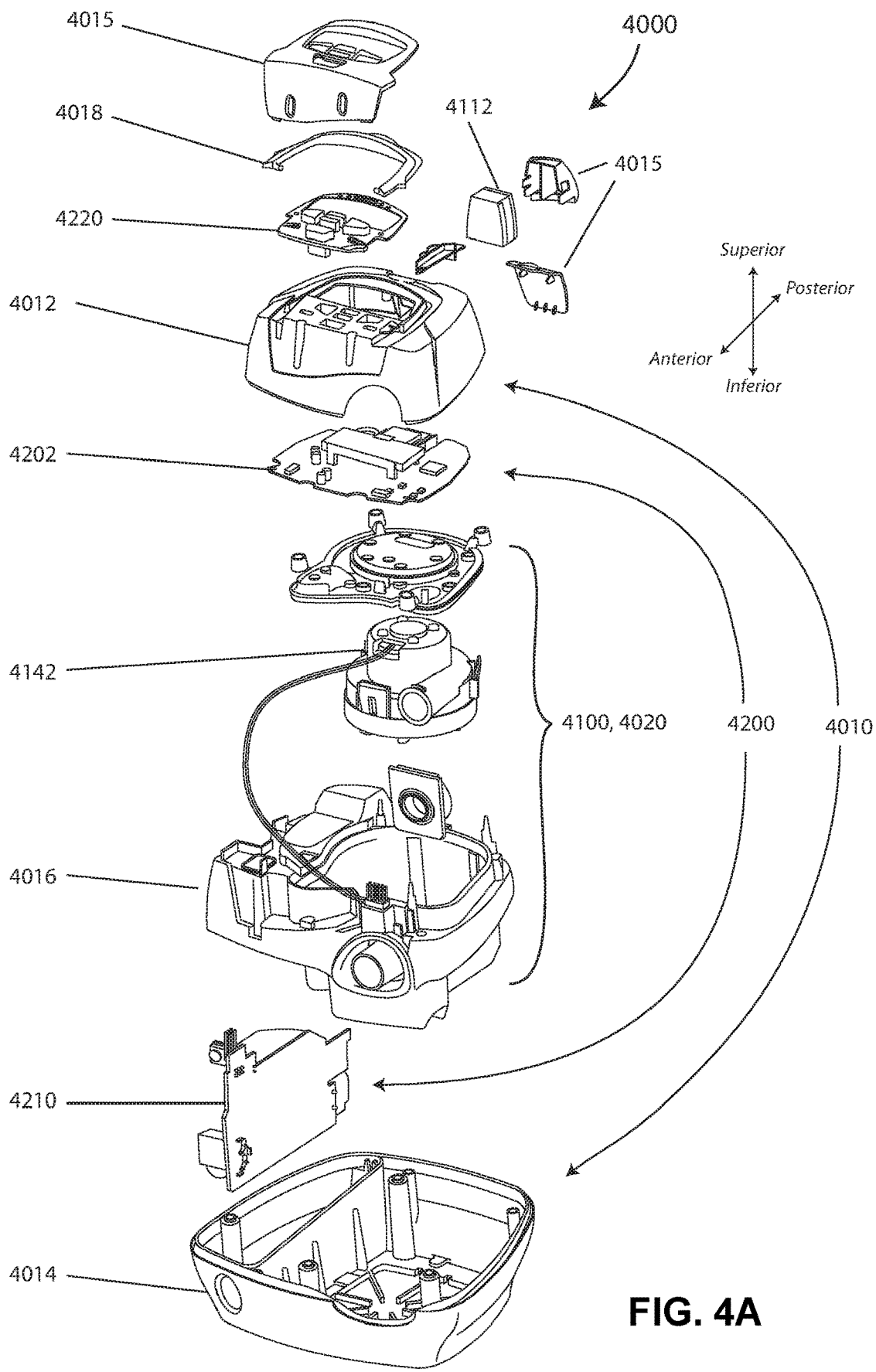
FIG. 4A shows an RPT device in accordance with one form of the present technology.
Figure 4B:
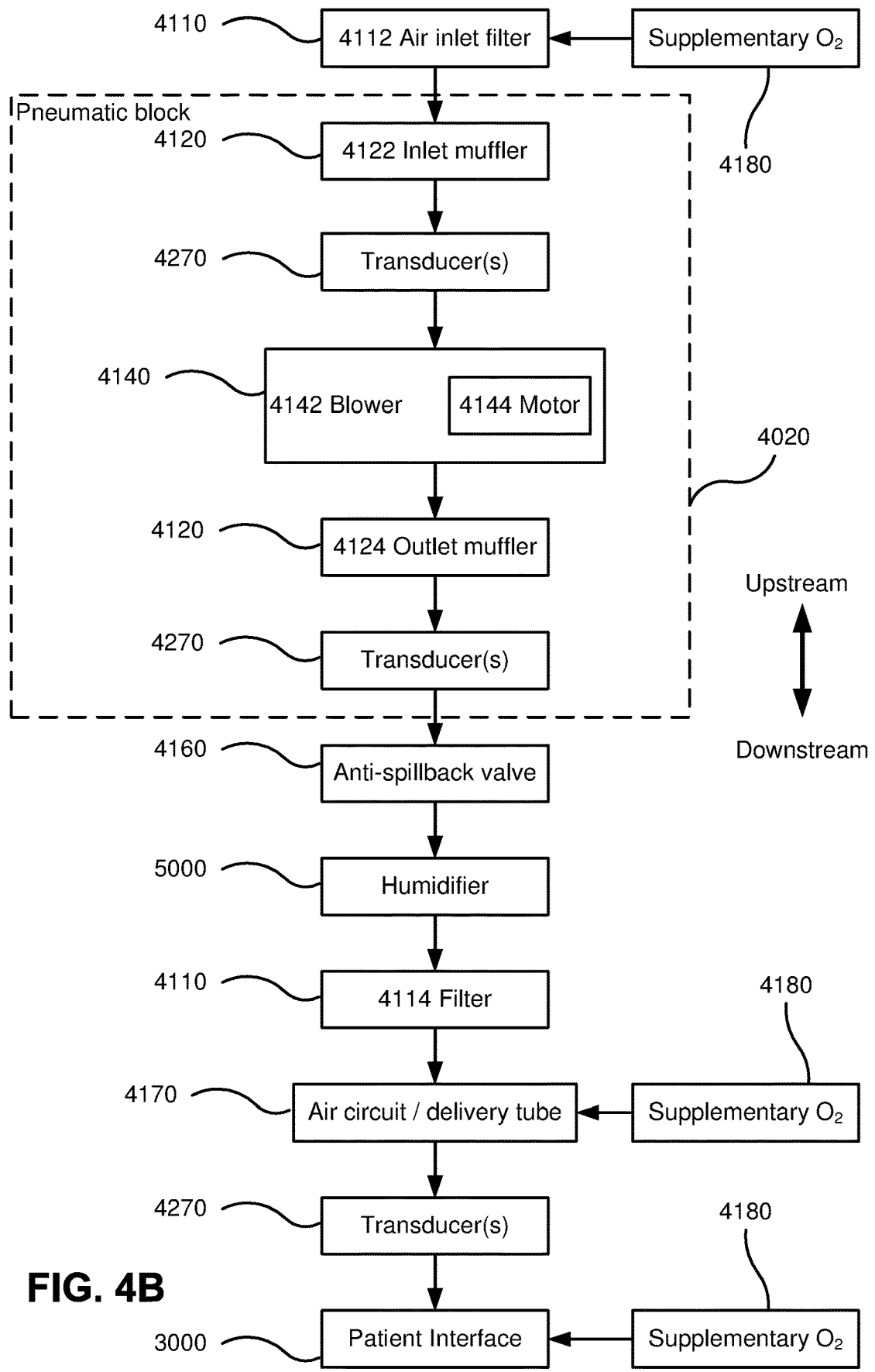
FIG. 4B is a schematic diagram of the pneumatic path of an RPT device in accordance with one form of the present technology. The directions of upstream and downstream are indicated.
Figure 4C:
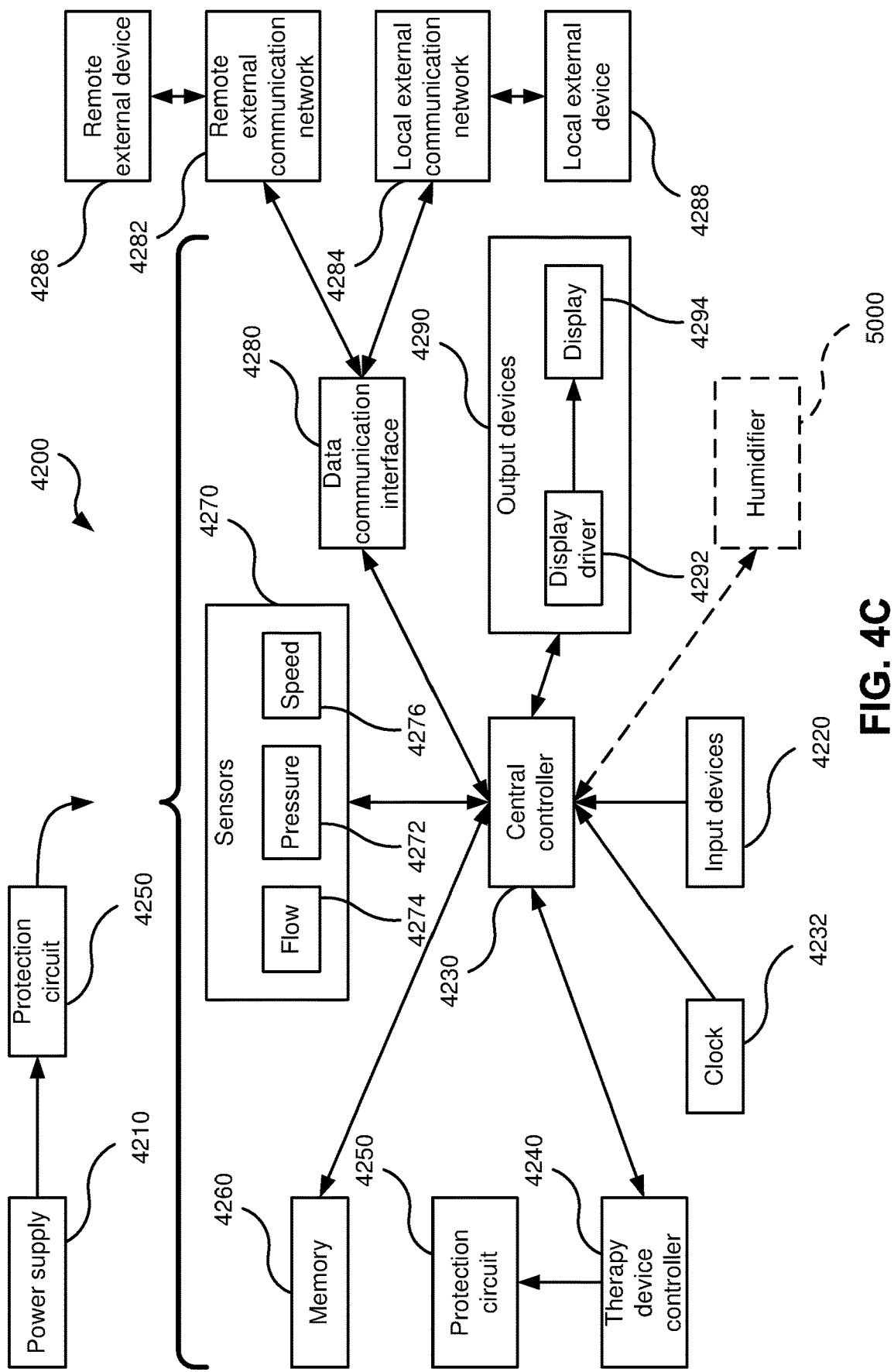
FIG. 4C is a schematic diagram of the electrical components of an RPT device in accordance with one form of the present technology.
Figure 8:
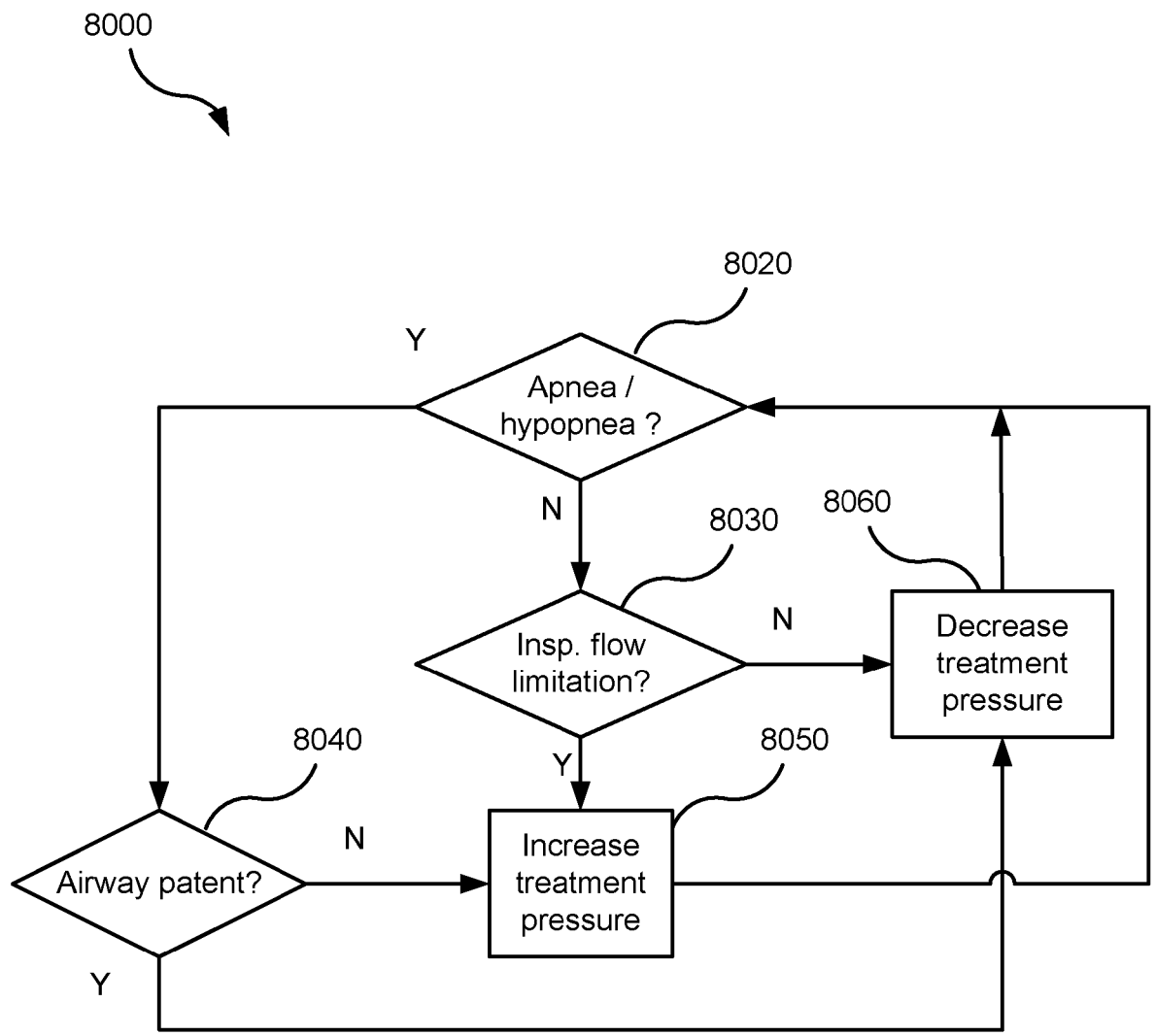

FIG. 8 contains a flow chart illustrating a method carried out by the central controller of the RPT device of FIG. 1 to adjust the treatment pressure after each breath as part of an APAP therapy mode to treat a patient's SDB.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

In one form, the present technology comprises a method for treating SDB comprising applying positive pressure to the entrance of the airways of a patient 1000. In certain examples of the present technology, a supply of air at positive pressure is provided to the nasal passages of the patient via one or both nares.

In some implementations of this form of the present technology, the treatment pressure Pt is approximately constant throughout the respiratory cycle. Such implementations are generally grouped under the heading of CPAP therapy. In CPAP therapy modes, the treatment pressure Pt may be a constant value that is hard-coded or manually entered to the RPT device 4000. This alternative is sometimes referred to as constant CPAP therapy.

Alternatively, the treatment pressure Pt may be automatically adjustable, e.g. from breath to breath, as a function of indicators or measures of SDB events such as flow limitation, apnea, hypopnea, patency, and snore. This alternative is sometimes referred to as APAP therapy.

8.2 Treatment Systems

In one form, the present technology comprises a system for treating SDB. The system may comprise an RPT device 4000 configured to supply pressurised air to the patient 1000 via an air circuit 4170 to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 RPT Device

An RPT device 4000 in accordance with one aspect of the present technology comprises mechanical and pneumatic components 4100, electrical components 4200 and is configured to execute one or more algorithms. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device may comprise one or more of the following components in an integral unit. In an alternative form, one or more of the following components may be located as respective separate units.

8.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

8.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

8.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. No. 7,866,944; U.S. Pat. No. 8,638,014; U.S. Pat. No. 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.4 Transducer(s)

Transducers may be internal of the RPT device, or external of the RPT device. External transducers may be located for example on or form part of the air circuit, e.g., the patient interface. External transducers may be in the form of noncontact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

8.4.1.4.1 Flow Rate Transducer

A flow rate transducer 4274 in accordance with the present technology may be based on a differential pressure transducer, for example, an SDP600 Series differential pressure transducer from SENSIRION.

In one form, a signal representing a flow rate such as a total flow rate Qt from the flow rate transducer 4274 is received by the central controller 4230.

8.4.1.4.2 Pressure Transducer

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

8.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

8.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

8.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

8.4.2 RPT Device Electrical Components
8.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

8.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

8.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier 5000.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

8.4.2.4 Clock

The RPT device 4000 may include a clock 4232 that is connected to the central controller 4230.

8.4.2.5 Therapy Device Controller

In one form of the present technology, therapy device controller 4240 is a control module that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits

The one or more protection circuits 4250 in accordance with the present technology may comprise an electrical protection circuit, a temperature and/or pressure safety circuit.

8.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein.

8.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

8.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.9.1 Display Driver

A display driver 4292 receives as an input the characters, symbols, or images intended for display on the display 4294, and converts them to commands that cause the display 4294 to display those characters, symbols, or images.

8.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.5 Humidifier

In one form of the present technology there is provided a humidifier 5000 (e.g. as shown in FIG. 5) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

8.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

FIG. 6B shows a patient during non-REM sleep breathing normally over a period of about ninety seconds, with about 34 breaths, being treated with APAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOGs (electro-oculograms). The sixth channel is an electocardiogram. The seventh channel shows pulse oximetry (SpO$_2$) with repetitive desaturations to below 70% from about 90%. The eighth channel is respiratory flow rate using a nasal cannula connected to a pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow rate data where the patient is experiencing a series of total obstructive apneas. The duration of the recording is approximately 160 seconds. Flow rates range from about +1 L/s to about −1.5 L/s. Each apnea lasts approximately 10 to 15 seconds.

FIG. 6E shows a scaled inspiratory portion of a breath where the patient is experiencing low frequency inspiratory snore.

FIG. 6F shows a scaled inspiratory portion of a breath where the patient is experiencing an example of flattened inspiratory flow limitation.

FIG. 6G shows a scaled inspiratory portion of a breath where the patient is experiencing an example of "mesa" flattened inspiratory flow limitation.

FIG. 6H shows a scaled inspiratory portion of a breath where the patient is experiencing an example of "panda ears" inspiratory flow limitation.

FIG. 6I shows a scaled inspiratory portion of a breath where the patient is experiencing an example of "chair" inspiratory flow limitation.

FIG. 6J shows a scaled inspiratory portion of a breath where the patient is experiencing an example of "reverse chair" inspiratory flow limitation.

FIG. 6K shows a scaled inspiratory portion of a breath where the patient is experiencing an example of "M-shaped" inspiratory flow limitation.

FIG. 6L shows a scaled inspiratory portion of a breath where the patient is experiencing an example of severely "M-shaped" inspiratory flow limitation.

8.7 Diagnosis/Monitoring Systems and Methods 8.7.1 Diagnosis/Monitoring Systems

FIG. 7B is a block diagram of a system 7000 for diagnosing or monitoring SDB in accordance with one form of the present technology. The system 7000 comprises a nasal cannula 7010. In use, the nasal cannula 7010 is inserted non-invasively a little way into the nares of the patient 1000. The nasal cannula 7010 is in fluid communication with a pressure transducer 7020, which generates a signal representative of the pressure at the prongs of the nasal cannula 7010. The generated pressure signal therefore represents the nasal pressure of the patient 1000. As mentioned above, a nasal pressure signal is a satisfactory proxy for the nasal flow rate of the patient 1000, which in turn is equal to the respiratory flow rate if the patient's mouth is kept closed. "Respiratory flow rate signal" will therefore be taken hereafter to include a nasal pressure signal from a nasal cannula such as the nasal cannula 7010. The system 7000 may also include a recording device 7030 configured to record the nasal pressure signal generated by the pressure transducer 7020 throughout a session, and to play back the recorded pressure signal for later diagnosis. The system 7000 also comprises a computing device 7040 that is configured to carry out the diagnosis on the nasal pressure signal, either recorded (diagnosis) or in real time (monitoring) according to a method described below.

An alternative system for diagnosing or monitoring SDB according to another form of the present technology comprises an SDB treatment system such as that illustrated in FIG. 1, comprising an RPT device 4000, an air circuit 4170, a humidifier 5000, and a patient interface 3000. In one implementation, the RPT device 4000 is configured not to deliver any respiratory pressure therapy, but simply to monitor the SDB of the patient 1000 during a session, or to diagnose the SDB of the patient 1000 afterwards. In other implementations, the RPT device 4000 is configured to deliver respiratory pressure therapy to the patient 1000 and to monitor the SDB of the patient 1000 during a treatment session, or to diagnose the SDB of the patient 1000 afterwards. In all such implementations, the RPT device 4000 is configured to calculate a respiratory flow rate signal Qr from the flow rate signal generated by the flow rate transducer 4274. The RPT device 4000 may also be configured to record the calculated respiratory flow rate signal Qr to the memory 4260 throughout a session, for later diagnosis.

8.7.2 Diagnosis/Monitoring Method

FIG. 7C is a flow chart illustrating a method 7100 according to one form of the present technology. The method 7100 may be carried out by the computing device 7040 of the system 7000 of FIG. 7B, in which case it is applied to a respiratory flow rate signal provided by the pressure transducer 7020, or by the central controller 4230 of an RPT device 4000, in which case is applied to a respiratory flow rate signal calculated by the central controller 4230, or by a remotely located computing device.

The method 7100 may be used as a diagnosis method, in which case it is applied after a session to a respiratory flow rate signal recorded during the session, or as a monitoring method, in which case it is applied during a session to a respiratory flow rate signal, in or near real time.

The output of the method 7100 is a metric indicating the degree of inspiratory flow limitation experienced by the patient 1000 during a session or an interval or sub-session thereof. In one implementation, the metric is a Boolean indicator, with a "true" value indicating the patient 1000 experienced significant flow limitation during the interval, and a "false" value indicating the opposite. In other implementations, the metric is continuously valued, indicating the degree of inspiratory flow limitation experienced by the patient 1000 during the interval.

Steps 7110, 7120 and 7130 of the method 7100 are carried out for each breath extracted from the respiratory flow rate signal by a "breath framing" process. A conventional breath framing process may be employed for this purpose.

Step 7110 extracts an inspiratory portion of the flow rate waveform of the current breath. The result of step 7110 is an inspiratory portion such as the inspiratory portion 7200 illustrated in FIG. 7D. Step 7110 may include resampling to ensure that the inspiratory portion consists of a predetermined number of samples. In one example, the predetermined number is 300.

Step 7120 calculates a feature vector representative of the inspiratory portion. Several implementations of step 7120 are described below, each of which calculates a different representation of the inspiratory portion: Difference-based Local Binary Patterns (DLBPs), non-negative matrix factorisation (NMF), and difference filtering (DF).

Human experts detect IFL based on the general shape of the inspiratory portion. The key shapes are different forms of flattening, namely common flattening as illustrated in FIGS. 6F, 6G, and 6H, "chair" and "reverse chair" as illustrated in FIGS. 6I and 6J, and "M shape" as illustrated in FIG. 6K and 6L. As features previously applied to IFL detection, such as power spectral density (PSD) features, are designed for different purposes, they generally extract irrelevant information. The three representations mentioned above are designed to only extract the general shape of the inspiratory portion and especially focus on flattening, while discarding the irrelevant detail information. In particular, DLBP only measures the occurrences of different forms of local flattening. Both NMF and DF represent the inspiratory portion using some "prototype shapes". For NMF representations, the "prototype shapes" are learned from examples. For DF representations, the "prototype shapes" are predefined.

Next, step 7130 applies a binary classifier to the calculated feature vector to label the inspiratory portion as flow limited or not flow limited. Various binary classifiers may be used to implement step 7130 including linear classifiers, neural networks, and decision trees. Different machine learning methods may be used to train a binary classifier based on training inspiratory portions that have been labelled as flow limited or not flow limited either by human experts or by an automatic effort/flow rate classification method that has access to an inspiratory effort waveform associated with each inspiratory portion. In one implementation, the binary classifier is trained by a Support Vector Machine (SVM). In this implementation, the support vector machine constructs a hyperplane to separate the positive training examples (feature vectors of inspiratory portions to be labelled as flow limited) and negative training examples (feature vectors of inspiratory portions to be labelled as normal) with maximum functional margin (the largest distance to the nearest training example of any class) in a high- or infinite-dimensional space. The hyperplane is then used as the binary classifier to label new feature vectors.

An alternative training strategy for a classifier is exhaustive training. An exhaustive training strategy traverses the entire space of the parameters of the hyperplane to find the hyperplane that most accurately classifies the training set. However, as the size of the training set increases, an exhaustive approach becomes prohibitively expensive in terms of computation. Another alternative training strategy for a classifier is one of finding a local optimum of an objective function over the parameter space. The objective function can be defined to maximize the margin over the hyperplane coefficients and minimize an estimate of the generalization error over the set of parameters. The optimization of the objective function can be solved using a gradient descent approach. As the local optimum is generally dependent on the starting point, the starting point may be optimised simultaneously with the hyperplane parameters.

The locally optimising parameters are also dependent on the feature representation used at step 7120. In an extension of the local optimisation strategy, the local optimisation is conducted multiple times in alternation with adjustments to the feature representation. This strategy tends to converge on a joint optimisation of the classifier and the feature representation.

In other implementations, other machine learning methods such as Adaboost, Linear Discriminant Analysis, Quadratic Discriminant Analysis, Naive Bayesian, Perceptron, and logistic regression may be used to train the binary classifier.

Finally, step 7140 computes a metric indicating the degree of inspiratory flow limitation being experienced by the patient 1000, based on the labels of inspiratory portions applied by the labelling step 7130. Step 7140 need not be carried out on every breath, which is why it is illustrated in dashed form, but may be carried out at multi-breath intervals on the labels applied to the breaths, or more strictly the inspiratory portions of the breaths, during the interval. If the multi-breath interval comprises the entire session, the method 7100 may be referred to as a diagnosis method; for shorter intervals, the method 7100 may be referred to as a monitoring method, in which case the metric may be reported in real time.

In some implementations of step 7140, the metric is continuously valued. In one such implementation of step 7140, the continuously-valued metric is a percentage or fraction of the total number of breaths in the interval that were labelled as flow limited. In other such implementations of step 7140, the continuously-valued metric may be:
- the average rate of flow-limited breaths (e.g. number per hour)
- the maximum rate of flow-limited breaths
- the average time interval between two flow-limited breaths
- a histogram of the numbers of consecutive flow-limited breaths in "max hour" (the hour in which the maximum number of flow-limited breaths occurred)
- a histogram of time intervals between two flow-limited breaths in "max hour"

In other implementations, step 7140 computes a continuously-valued metric as described above, and then computes a Boolean result of comparing the continuously-valued metric with a threshold. If the continuously-valued metric is greater than the threshold, the Boolean result is "true" indicating the patient 1000 experienced significant inspiratory flow limitation during the interval; otherwise the Boolean result is "false".

8.7.2.1 DLBP Representation

The DLBP representation is intended to concentrate on the flattening of the inspiratory portion. To calculate the DLBP feature vector of an inspiratory portion, step 7120 compares each of the samples of the inspiratory portion with its neighbouring samples and assigns a DLBP code to each sample based on the differences. In one implementation, the DLBP code for the sample x[i], which is the i-th sample from an inspiratory portion x of length N samples, may be calculated as follows:

$$DLBP_{p,v,t}(x[i]) = \sum_{r=0}^{\frac{p}{2}-1} \left\{ \begin{array}{l} S_t\left(\left|x\left[i + \left(r - \frac{p}{2}\right)v\right] - x[i]\right|\right)2^{p-r-1} + \\ S_t(|x[i + (r+1)v] - x[i]|)2^{\frac{p}{2}-r-1} \end{array} \right\}$$

where:
p is the (even) total number of neighbouring samples around the sample x[i], so that p/2 neighbouring samples on each side of x[i] contribute to the DLBP of x[i];
v is the neighbourhood sampling interval;
t is a threshold; and
$S_t$ is a thresholding function that is 0 if its argument is less than t, and 1 otherwise.

The DLBP code for the sample x[i] is an integer from 0 to $2^p-1$. DLBP codes of an inspiratory portion x of N samples are defined on samples x[i] from i=1+pv/2 to N-pv/2, so there are N-pv DLBP codes for an N-sample inspiratory portion.

In one implementation, values for p, v, and t are 8, 2, and 0.003. For these values, DLBP codes are defined on samples x[i] from i=9 to N-8, so there are N-16 DLBP codes for an N-sample inspiratory portion.

An inspiratory portion x may be represented by a histogram of the DLBP codes $DLBP_{p,v,t}(x[i])$ of its samples x[i]. In one implementation of the DLBP representation, the DLBP feature vector calculated at step 7120 is a vector of $2^p$ DLBP histogram values H(q) for q=0 to $2^p-1$, where H(q) is the number of samples x[i] whose DLBP code $DLBP_{p,v,t}(x[i])$ is equal to q.

A perfectly flat inspiratory portion (x[i]=a constant for all i) has all DLBP codes equal to zero, so the histogram values are all zero except H(0), which is equal to N-pv. A "noise" inspiratory portion will on the other hand have most DLBP codes equal to $2^p-1$, so most histogram values will be zero except $H(2^p-1)$, which will be close to N-pv.

The DLBP histogram representation extracts not only the shape but also the time series information of inspiratory portions, especially focusing on flattening, which is a key feature of flow-limited inspiratory signals. FIG. 7D shows an inspiratory portion 7200 with flow limitation, and an inspiratory portion 7210 of a normal breath. FIG. 7E shows the DLBP histogram 7220 (with p=8) of the flow-limited inspiratory portion 7200, and FIG. 7F shows the DLBP histogram 7230 of the normal inspiratory portion 7210. FIGS. 7E and 7F show that the DLBP histogram for flow-limited inspiratory portions is clearly different from the DLBP histogram for normal breaths.

FIGS. 7E and 7F also show that DLBP histograms are sparse. Therefore, in some implementations of the DLBP representation, only selected bins of the DLBP histogram appear in the DLBP feature vector. In such implementations, bins that always contain zero occurrences are discarded from the DLBP feature vector. In one such implementation (p=8, v=8, t=0.003), 99 bins (out of 256 bins in total) appear in the DLBP feature vector.

8.7.2.2 NMF Representation

The non-negative matrix factorization (NMF) representation extracts the shape information of inspiratory portions. Given a non-negative "database" matrix V with m rows and n columns, NMF finds non-negative matrices W (m by r) and H (r by n) such that V is approximated by the product WH. The rank r of the factorization is generally chosen to satisfy (n+m)r<mn, so that the product WH can be regarded as a compressed form of the data in the matrix V.

NMF may be regarded as a non-negative approximate signal representation. To apply NMF to signal representation, a set of n signal vectors, each of length m samples, is concatenated into the database matrix V, where each column of V is one of the signal vectors. NMF approximately factorises V into a left factor matrix W and a right factor matrix H:

$$V \approx WH \quad (2)$$

Each signal vector (column) in V can be approximated as a linear combination of r basis vectors, also of length m, namely the columns of the factor matrix W. The r coefficients of the linear combination make up the corresponding column of the factor matrix H. The r coefficients in each column of H describe how strongly each basis vector is present in the signal vector in the corresponding column of V.

Given a signal database matrix V, NMF finds W and H to minimise the reconstruction error between V and WH, which is typically represented by the Euclidean distance. This minimization problem is not convex with respect to both W and H, but it is convex with respect to each variable separately. In one implementation of NMF, the multiplicative algorithm devised by Lee and Seung [1] may be used to find a "locally" optimal pair W, H.

Several variant implementations of NMF have been proposed to improve NMF from different perspectives. One variant NMF implementation called local NMF (LNMF) [2] enforces the maximum sparsity of H and the maximum orthogonality of W. Another variant NMF implementation explicitly constrains the sparsity of W and H and is thus named NMFsc (NMF with sparsity constraints) [3]. Both of these variant implementations focus on locality of the NMF basis vectors, and are therefore suitable for the present classification task, as the local flattening of signals is a key feature to differentiate flow-limited inspiratory portions from normal ones.

To calculate the NMF representation, the matrices W and H are first computed from a database matrix V of n inspiratory portions, each with the same number m of samples, using one of the above-described implementations.

To calculate the NMF representation of an inspiratory portion x (resampled to m samples if necessary), step 7120 calculates a feature vector h as the r coefficients of the inspiratory portion x obtained by multiplying the inspiratory portion x by the pseudoinverse $W^{pinv}$ of W:

$$h = W^{pinv} x \quad (3)$$

In one implementation, $W^{pinv}$ is the left inverse $W_{left}^{-1}$ of W, computed as $$W_{left}^{-1} = (W^T W)^{-1} W^T \quad (4)$$

Other implementations use other pseudoinverses such as the Moore-Penrose pseudoinverse to compute the feature vector h.

FIG. 7G shows a set 7300 of basis vectors of length m=300 obtained using NMFsc on the test data set of n=2312 inspiratory portions described below, where the rank r (the number of basis vectors in the set 7300) is set to 81, the sparsity of W (sW) is set to 0.2, and the sparsity of H (sH) is set to 0.8.

FIG. 7H shows an example inspiratory portion 7400 of length m=300, and FIG. 7I is a plot of the r=81 coefficients 7410 of the inspiratory portion 7400 using the set 7300 of 81 basis vectors shown in FIG. 7G. The coefficients 7410 are sparse, only 9 of them being non-zero.

8.7.2.3 DF Representation

The DF representation is based on a set of difference filters designed to extract the shape and time series information of inspiratory portions. Each difference filter yields one feature in the DF feature vector. The difference filters are binary-valued (either 1 or −1) with the same number of coefficients as the inspiratory portion has samples. The DF feature vector can therefore be calculated at extremely low computational cost as it only requires additions and subtractions.

Step 7120 calculates each feature in the DF feature vector by summing the samples of the inspiratory portion with a weighting of either +1 or −1, wherein the weightings are coefficients of the corresponding difference filter.

In one implementation of the DF representation, 25 difference filters are used, so the DF representation is a vector of length 25. Each of the 25 difference filters may be represented as a series of integers indicating the lengths of alternating sequences of +1 and −1 as a proportion of the length of the difference filter. For example, the series 1:1 indicates that the difference filter coefficients are divided into two halves, the first being equal to +1, and the second being equal to −1. The 25 filters are as represented by the following 25 series:

1:1 (halves)
1:2, 1:1:1, 2:1 (thirds)
1:3, 1:1:2, 2:1:1, 3:1, 1:2:1, 1:1:1:1 (quarters)
1:4, 1:1:3, 2:1:2, 3:1:1, 4:1, 2:3, 1:2:2, 2:2:1, 3:2, 1:1:1:2,
    1:2:1:1, 1:3:1, 1:1:1:1:1, 1:1:2:1, 2:1:1:1 (fifths)

FIG. 7J shows an example normal inspiratory portion 7500 and a flow-limited inspiratory portion 7510. FIG. 7K is a plot of the 25 entries of the DF feature vectors 7520 and 7530 of the inspiratory portions 7500 and 7510 using the 25 difference filters described above. FIGS. 7J and 7K show that the DF feature vector 7530 for the flow-limited inspiratory portion 7510 is clearly different from the DF feature vector 7520 for the normal inspiratory portion 7500.

8.7.3 Example Results

A test dataset contained three 100-minute recordings of respiratory flow signals from sleeping pregnant women. Each inspiration portion in the test dataset was labelled as flow limited, intermediate, or not flow limited by three human experts using criteria collaboratively developed by researchers at McGill and Harvard Universities. The sampling frequency of the recordings was 256 Hz. The majority opinion from the three scorers was used as the "ground truth" for each inspiratory portion in the analysis period. In total, there were 1754 flow-limited inspiratory portions and 558 non-flow-limited inspiratory portions in the test dataset (so n=2312). The intermediate-labelled inspiratory portions were discarded.

Tenfold cross-validation was conducted for all the disclosed implementations of the method 7100 on the test dataset. The best results achieved are reported in Table 1, with corresponding parameters. As can be seen from Table 1, all five implementations performed objectively well. The LNMF representation achieved the best specificity, while the DLBP representation achieved the best sensitivity and overall accuracy.

TABLE 1

Results for tenfold cross-validation

| Imp | Sens | Spec | Accuracy | Parameters |
| --- | --- | --- | --- | --- |
| DLBP | 0.87 | 0.93 | 0.90 | p = 8, v = 7, t = 0.003 |
| NMF | 0.69 | 0.96 | 0.82 | r = 121, m = 300 |
| LNMF | 0.70 | 0.97 | 0.84 | r = 200, m = 300 |
| NMFsc | 0.73 | 0.96 | 0.84 | r = 64, m = 300, sW = 0.2, sH = 0.8 |
| DF | 0.75 | 0.95 | 0.85 | 25 difference filters |

8.8 Treatment Methods

In addition to forming part of the method 7100 described above, the labelling of an inspiratory portion of each breath as flow limited or not flow limited, as implemented by steps 7110 to 7130 of the method 7100, may be used in real time as part of treating a patient's SDB.

FIG. 8 contains a flow chart illustrating a method 8000 that may be carried out by the central controller 4230 of the RPT device 4000 to adjust the treatment pressure Pt after each breath as part of an APAP therapy mode to treat a patient's SDB.

The method 8000 starts at step 8020, at which the central controller 4230 determines whether an apnea or a hypopnea is occurring. Conventional apnea/hypopnea detection methods based on the respiratory flow rate Qr may be used to implement step 8020. If so ("Y"), the method 8000 proceeds to step 8040; otherwise ("N"), the method 8000 proceeds to step 8030. At step 8040, the central controller 4230 determines whether the airway is patent. If so ("Y"), the method 8000 proceeds to step 8060; otherwise ("N"), the apnea/hypopnea is deemed obstructive, and the method 8000 proceeds to step 8050.

At step 8030, the central controller 4230 determines whether the inspiratory portion is flow limited. In one implementation, steps 7110 to 7130 of the method 7100 described above may be used to implement step 8030. If so ("Y"), the method 8000 proceeds to step 8050; otherwise ("N"), the method 8000 proceeds to step 8060.

At step 8050, the central controller 4230 increases the treatment pressure Pt by a predetermined pressure increment ΔP, provided the resulting treatment pressure Pt would not exceed a maximum treatment pressure Pmax. In one implementation, the predetermined pressure increment ΔP and maximum treatment pressure Pmax are 1 $cmH_2O$ and 25 $cmH_2O$ respectively. In other implementations, the pressure increment ΔP can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 8000 then returns to step 8020.

At step 8060, the central controller 4230 decreases the treatment pressure Pt by a decrement, provided the resulting treatment pressure Pt would not fall below a minimum treatment pressure Pmin. The method 8000 then returns to step 8020. In one implementation, the decrement is proportional to the value of Pt−Pmin, so that the decrease in the treatment pressure Pt to the minimum treatment pressure Pmin in the absence of any detected events is exponential. In one implementation, the constant of proportionality is set such that the time constant of the exponential decrease of the treatment pressure Pt is 60 minutes, and the minimum treatment pressure Pmin is 4 $cmH_2O$. In other implementations, the time constant could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in the treatment pressure Pt could be predetermined, so the decrease in Pt to the minimum treatment pressure Pmin in the absence of any detected apnea/hypopnea or flow-limited inspiratory portion is linear.

8.9 Glossary

For the purposes of the present technology disclosure, in certain forms of the present technology, one or more of the following definitions may apply. In other forms of the present technology, alternative definitions may apply.

8.9.1 General

Air: In certain forms of the present technology, air may be taken to mean atmospheric air, and in other forms of the present technology air may be taken to mean some other combination of breathable gases, e.g. atmospheric air enriched with oxygen.

Continuous Positive Airway Pressure (CPAP) therapy: Respiratory pressure therapy in which the pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Respiratory Pressure Therapy (RPT): The application of a supply of air to an entrance to the airways at a treatment pressure that is typically positive with respect to atmosphere.

8.9.2 Aspects of the Respiratory Cycle

Apnea: Preferably, apnea will be said to have occurred when flow falls below a predetermined threshold rate for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Apnea-Hypopnea Index (AHI): The number of apnea or hypopneas undergone by a patient, on average, per hour. AHI is a generally accepted measure of the severity of a patient's OSA.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: The state of affairs in a patient's respiration whereby an increase in effort by the patient does not give rise to a corresponding increase in flow. Where flow limitation occurs during an inspiratory portion of the breathing cycle it may be described as inspiratory flow limitation (IFL). Where flow limitation occurs during an expiratory portion of the breathing cycle it may be described as expiratory flow limitation (EFL).

Types of flow-limited inspiratory portions:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

8.9.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of unintentional leak from a patient interface system. Respiratory flow rate, Qr, is the flow rate of air that is received into the patient's respiratory system.

Leak: The word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

8.9.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.11 Reference Signs List patient 1000
bed partner 1100
headbox 2000 ground electrode 2010
EOG electrode 2015
EEG electrode 2020
ECG electrode 2025
submental EMG electrode 2030
snore sensor 2035
respiratory inductance plethysmogram 2040
respiratory inductance plethysmogram 2045
cannula 2050
photoplethysmograph 2055
body position sensor 2060
patient interface 3000
seal-forming structure 3100
plenum chamber 3200
structure 3300
vent 3400
connection port 3600
forehead support 3700
RPT device 4000
external housing 4010
upper portion 4012
portion 4014
panel 4015
chassis 4016
handle 4018
pneumatic block 4020
pneumatic components 4100
air filters 4110
inlet air filter 4112
outlet air filter 4114
mufflers 4120
inlet muffler 4122
outlet muffler 4124
pressure generator 4140
blower 4142
motor 4144
anti-spill back valve 4160
air circuit 4170
supplemental oxygen 4180
electrical components 4200
PCBA 4202
electrical power supply 4210
input device 4220
central controller 4230
clock 4232
therapy device controller 4240
protection circuits 4250
memory 4260
transducers 4270
pressure transducer 4272
flow rate transducer 4274
motor speed transducer 4276
data communication interface 4280
remote external communication network 4282
local external communication network 4284
remote external device 4286
local external device 4288
output devices 4290
display driver 4292
display 4294
humidifier 5000
system 7000
nasal cannula 7010
pressure transducer 7020
recording device 7030
device 7040
method 7100
step 7110
step 7120
step 7130
step 7140
flow-limited inspiratory portion 7200
normal inspiratory portion 7210
DLBP histogram 7220
DLBP histogram 7230
set 7300
example inspiratory portion 7400
coefficients 7410
inspiratory portions 7500
inspiratory portions 7510
DF feature vector 7520
DF feature vector 7530
method 8000
step 8020
step 8030
step 8040
step 8050
step 8060

9 CITATIONS

[1] Daniel D. Lee and H. Sebastian Seung. *Algorithms for non-negative matrix factorization.* Proceedings of NIPS 2000, pages 556-562, 2000.

[2] Stan Z. Li, Xinwen Hou, Hongjiang Zhang, and Qian-Sheng Cheng. *Learning spatially localized, parts-based representation.* Proceedings of CVPR '01, volume 1, pages 207-212, 2001.

[3] Patrik O. Hoyer. *Non-negative matrix factorization with sparsity constraints.* The Journal of Machine Learning Research, 5(5):1457-1469, 2004.

The invention claimed is:

1. A method comprising:
    extracting, with one or more processors, inspiratory portions of breaths of a patient from respiratory flow rate signals generated by a flow rate sensor;
    extracting, with the one or more processors, shape information from the inspiratory portions;
    calculating, with the one or more processors, difference-based local binary pattern (DLBP) feature vectors representative of the inspiratory portions, wherein the calculating comprises:
        comparing each of a plurality of samples of the inspiratory portions with adjacent samples to determine differences between the samples, and
        assigning a DLBP code to each of the samples of the inspiratory portions based on the differences;
    applying, with the one or more processors, labels to the inspiratory portions based on the DLBP feature vectors, wherein the labels indicate whether the inspiratory portions are flow limited;
    computing, with the one or more processors, a metric indicating a degree of inspiratory flow limitation of the patient based on the labels applied to the inspiratory portions; and
    adjusting, with the one or more processors, a treatment pressure of a respiratory pressure therapy being delivered to the patient by a respiratory pressure therapy device based on the labels applied to the inspiratory portions.

2. A method according to claim 1, wherein the DLBP feature vectors are vectors of histogram values of the DLBP codes assigned to the samples of the inspiratory portions.

3. A method according to claim 2, wherein the DLBP code is an integer.

4. A method according to claim 1, wherein applying the labels to the inspiratory portions comprises applying a binary classifier to the DLBP feature vectors.

5. A method according to claim 4, wherein the binary classifier is a linear classifier.

6. A method according to claim 4, wherein the binary classifier has been trained using a Support Vector Machine and a plurality of labelled inspiratory portions.

7. A method according to claim 4, wherein the binary classifier has been trained by optimising an objective function over a parameter space of the classifier.

8. A method according to claim 1, wherein the metric is a fraction of a total number of the breaths having an inspiratory portion to which a label has been applied that indicates the inspiratory portion is flow limited.

9. A method according to claim 1, wherein the metric is an average rate of the breaths having an inspiratory portion to which a label has been applied that indicates the inspiratory portion is flow limited.

10. A method according to claim 1, wherein the metric is a maximum rate of the breaths having an inspiratory portion to which a label has been applied that indicates the inspiratory portion is flow limited.

11. A method according to claim 1, further comprising comparing the metric with a threshold.

12. A system comprising:
a flow rate sensor configured to generate signals representing a respiratory flow rate of a patient; and
a computing device including one or more processors, the computing device configured to:
extract inspiratory portions of breaths of a patient from the generated respiratory flow rate signals,
extract shape information from the inspiratory portions,
calculate difference-based local binary pattern (DLBP) feature vectors representative of the inspiratory portions, wherein the calculating comprises:
comparing each of a plurality of samples of the inspiratory portions with adjacent samples to determine differences between the samples, and
assigning a DLBP code to each of the samples of the inspiratory portions based on the differences,
apply labels to the inspiratory portions based on the DLBP feature vectors, wherein the labels indicate whether the inspiratory portions are flow limited,
compute a metric indicating a degree of inspiratory flow limitation of the patient based on the labels applied to the inspiratory portions, and
adjust a treatment pressure of a respiratory pressure therapy being delivered to the patient by a respiratory pressure therapy device based on the labels applied to the inspiratory portions.

13. A system according to claim 12, further comprising a recording device configured to record the generated respiratory flow rate signals.

14. A system according to claim 12, wherein the flow rate sensor comprises a nasal cannula in communication with a pressure transducer, and the generated respiratory flow rate signals are nasal pressure signals generated by the pressure transducer.

15. A system according to claim 12, wherein the computing device comprises a controller of the respiratory pressure therapy device configured to deliver respiratory pressure therapy to the patient.

16. A method comprising:
extracting inspiratory portions of breaths of a patient from respiratory flow rate signal of the patient signals generated by a flow rate sensor;
extract shape information from the inspiratory portions;
calculating difference-based local binary pattern (DLBP) feature vectors representative of the inspiratory portions, wherein the calculating comprises:
comparing each of a plurality of samples of the inspiratory portions with adjacent samples to determine differences between the samples, and
assigning a DLBP code to each of the samples of the inspiratory portions based on the differences,
apply labels to the inspiratory portions based on the DLBP feature vectors, wherein the labels indicate whether the inspiratory portions are flow limited, and
controlling adjustment of a treatment pressure of respiratory pressure therapy being delivered to the patient by a respiratory pressure therapy device based on the labels applied to the inspiratory portions.

17. A method according to claim 16, wherein the adjustment comprises increasing the treatment pressure of the respiratory pressure therapy device upon an inspiratory portion being labelled as flow limited.

18. A system comprising:
a respiratory pressure therapy device configured to deliver respiratory pressure therapy to a patient via a patient interface over an air circuit, the patient interface configured to sealingly engage an entrance to an airway of the patient, the air circuit in communication with the patient interface, the respiratory pressure therapy device comprising:
a pressure generator configured to generate a supply of air at positive pressure to the air circuit;
a flow rate sensor configured to generate signals representing a respiratory flow rate of the patient; and
a controller configured to:
extract inspiratory portions of a breaths of the patient from the generated respiratory flow rate signals,
extract shape information from the inspiratory portions,
calculate difference-based local binary pattern (DLBP) feature vectors representative of the inspiratory portions, wherein the calculating comprises:
comparing each of a plurality of samples of the inspiratory portions with adjacent samples to determine differences between the samples, and
assigning a DLBP code to each of the samples of the inspiratory portions based on the differences,
apply labels to the inspiratory portions based on the DLBP feature vectors, wherein the labels indicate whether the inspiratory portions are flow limited, and
control the pressure generator to adjust a treatment pressure of the respiratory pressure therapy based on the labels applied to the inspiratory portions.

19. The sleep disordered treatment system of claim 18 further comprising:
the patient interface configured to sealingly engage the entrance to the airway of the patient; and
the air circuit in communication with the patient interface.

20. A method according to claim 1, wherein the adjusting comprises:
increasing the treatment pressure in response to a label being applied to an inspiratory portion that indicates the inspiratory portion is flow limited; or
decreasing the treatment pressure in response to a label being applied to an inspiratory portion that indicates the inspiratory portion is not flow limited.

21. A method according to claim 1, further comprising: displaying, with an output device, the metric.

22. A method according to claim 1, wherein the flow rate sensor comprises a nasal cannula in communication with a pressure transducer, and wherein the respiratory flow rate signals are nasal pressure signals generated by the pressure transducer.

23. A method according to claim 1, wherein the shape information comprises occurrences of one or more forms of local flattening.

* * * * *